United States Patent
Adolphi et al.

(10) Patent No.: US 8,710,836 B2
(45) Date of Patent: Apr. 29, 2014

(54) NMR, INSTRUMENTATION, AND FLOW METER/CONTROLLER CONTINUOUSLY DETECTING MR SIGNALS, FROM CONTINUOUSLY FLOWING SAMPLE MATERIAL

(75) Inventors: Natalie Louise Adolphi, Albuquerque, NM (US); Andrew Frederick McDowell, Albuquerque, NM (US)

(73) Assignee: nanoMR, Inc., Albuquerque, NM (US)

( * ) Notice: Subject to any disclaimer, the term of this patent is extended or adjusted under 35 U.S.C. 154(b) by 786 days.

(21) Appl. No.: 12/635,583

(22) Filed: Dec. 10, 2009

(65) Prior Publication Data

US 2010/0141255 A1    Jun. 10, 2010

Related U.S. Application Data

(60) Provisional application No. 61/121,416, filed on Dec. 10, 2008.

(51) Int. Cl.
| | |
|---|---|
| G01R 33/32 | (2006.01) |
| G01R 33/563 | (2006.01) |
| G01N 24/08 | (2006.01) |
| G01R 33/30 | (2006.01) |

(52) U.S. Cl.
CPC ........ *G01R 33/563* (2013.01); *G01R 33/56375* (2013.01); *G01R 33/56383* (2013.01); *G01R 33/307* (2013.01); *G01R 33/32* (2013.01); *G01N 24/08* (2013.01); *G01N 24/085* (2013.01)
USPC ........... 324/306; 324/303; 324/321; 324/318; 324/307; 600/419

(58) Field of Classification Search
CPC .......... G01R 33/563; G01R 33/56375; G01R 33/56383; G01R 33/307; G01R 33/32; G01N 24/08; G01N 24/085
USPC .......................... 324/300–322; 600/407–435; 382/128–131
See application file for complete search history.

(56) References Cited

U.S. PATENT DOCUMENTS

| | | | |
|---|---|---|---|
| 2,973,471 A | * | 2/1961 | Armistead et al. ............ 324/303 |
| 3,970,518 A | | 7/1976 | Giaever |

(Continued)

FOREIGN PATENT DOCUMENTS

| | | |
|---|---|---|
| CA | 2342047 A1 | 9/2001 |
| EP | 1304581 A2 | 10/2002 |

(Continued)

OTHER PUBLICATIONS

Abragam, "Principles of Nuclear Magnetism," *Clarendon Press, Oxford*, 1961, pp. 71-83.

(Continued)

*Primary Examiner* — Melissa Koval
*Assistant Examiner* — Tiffany Fetzner
(74) *Attorney, Agent, or Firm* — Thomas C. Meyers; Brown Rudnick LLP

(57) ABSTRACT

NMR technology disclosed herein, such as an NMR apparatus or an NMR method, for example, may be useful for purposes described herein, such as determining presence or absence of magnetic resonance from a sample, for example. Methods pertaining to such NMR technology include methods of designing or constructing NMR apparatus, methods of using NMR apparatus, methods of employing data obtained from NMR apparatus, and/or the like. Various apparatus and methods for detection of magnetic resonance in sample material are disclosed herein. Additionally, various apparatus and methods for usefully employing magnetic resonance data are disclosed herein.

7 Claims, 14 Drawing Sheets

(56) References Cited

U.S. PATENT DOCUMENTS

| | | | |
|---|---|---|---|
| 4,018,886 A | 4/1977 | Giaever | |
| 4,230,685 A | 10/1980 | Senyei et al. | |
| 4,267,234 A | 5/1981 | Rembaum | |
| 4,452,773 A | 6/1984 | Molday | |
| 4,480,227 A * | 10/1984 | Brown | 324/303 |
| 4,551,435 A | 11/1985 | Liberti et al. | |
| 4,554,088 A | 11/1985 | Whitehead et al. | |
| 4,659,678 A | 4/1987 | Forrest et al. | |
| 4,677,055 A | 6/1987 | Dodin et al. | |
| 4,695,393 A | 9/1987 | Chagnon et al. | |
| 4,785,245 A * | 11/1988 | Lew et al. | 324/308 |
| 4,795,698 A | 1/1989 | Owen et al. | |
| 4,868,500 A * | 9/1989 | Baldwin et al. | 324/307 |
| 4,901,018 A | 2/1990 | Lew | 324/306 |
| 4,925,788 A | 5/1990 | Liberti | |
| 5,047,321 A | 9/1991 | Loken et al. | |
| 5,057,413 A | 10/1991 | Terstappen et al. | |
| 5,089,386 A | 2/1992 | Stackebrandt et al. | |
| 5,108,933 A | 4/1992 | Liberti et al. | |
| 5,136,095 A | 8/1992 | Tarnowski et al. | 565/286 |
| 5,164,297 A | 11/1992 | Josephson et al. | 435/7.25 |
| 5,186,827 A | 2/1993 | Liberti et al. | |
| 5,200,084 A | 4/1993 | Liberti et al. | |
| 5,229,724 A | 7/1993 | Zeiger | |
| 5,234,816 A | 8/1993 | Terstappen | |
| 5,254,460 A | 10/1993 | Josephson et al. | 435/7.25 |
| 5,338,687 A | 8/1994 | Lee et al. | 436/173 |
| 5,342,790 A | 8/1994 | Levine et al. | |
| 5,460,979 A | 10/1995 | Levine et al. | |
| 5,466,574 A | 11/1995 | Liberti et al. | |
| 5,512,332 A | 4/1996 | Liberti et al. | |
| 5,541,072 A | 7/1996 | Wang et al. | |
| 5,583,033 A | 12/1996 | Terstappen et al. | |
| 5,597,531 A | 1/1997 | Liberti et al. | |
| 5,605,805 A | 2/1997 | Verwer et al. | |
| 5,622,831 A | 4/1997 | Liberti et al. | |
| 5,622,853 A | 4/1997 | Terstappen et al. | |
| 5,646,001 A | 7/1997 | Terstappen et al. | |
| 5,654,636 A | 8/1997 | Sweedler et al. | 324/321 |
| 5,660,990 A | 8/1997 | Rao et al. | |
| 5,677,133 A | 10/1997 | Oberhardt | 435/7.1 |
| 5,681,478 A | 10/1997 | Lea et al. | |
| 5,684,401 A | 11/1997 | Peck et al. | 324/318 |
| 5,695,946 A | 12/1997 | Benjamin et al. | |
| 5,698,271 A | 12/1997 | Liberti et al. | |
| 5,741,714 A | 4/1998 | Liberti | |
| 5,768,089 A | 6/1998 | Finnigan | 361/287 |
| 5,770,461 A | 6/1998 | Sakazume et al. | |
| 5,773,307 A | 6/1998 | Colin et al. | 436/526 |
| 5,776,710 A | 7/1998 | Levine et al. | |
| 5,795,470 A | 8/1998 | Wang et al. | |
| 5,821,066 A | 10/1998 | Pyle et al. | |
| 5,834,217 A | 11/1998 | Levine et al. | |
| 5,840,580 A | 11/1998 | Terstappen et al. | |
| 5,866,099 A | 2/1999 | Owen et al. | |
| 5,876,593 A | 3/1999 | Liberti et al. | |
| 5,925,573 A | 7/1999 | Colin et al. | 436/525 |
| 5,948,412 A | 9/1999 | Murphy | |
| 5,985,153 A | 11/1999 | Dolan et al. | |
| 5,993,665 A | 11/1999 | Terstappen et al. | |
| 6,013,188 A | 1/2000 | Terstappen et al. | |
| 6,013,532 A | 1/2000 | Liberti et al. | |
| 6,060,882 A | 5/2000 | Doty | |
| 6,097,188 A | 8/2000 | Sweedler et al. | 324/321 |
| 6,120,856 A | 9/2000 | Liberti et al. | |
| 6,136,182 A | 10/2000 | Dolan et al. | |
| 6,177,798 B1 * | 1/2001 | Haner et al. | 324/321 |
| 6,194,900 B1 | 2/2001 | Freeman et al. | 324/321 |
| 6,228,624 B1 | 5/2001 | Terstappen | |
| 6,236,205 B1 | 5/2001 | Ludeke et al. | 324/318 |
| 6,242,915 B1 | 6/2001 | Hurd | 324/309 |
| 6,265,150 B1 | 7/2001 | Terstappen et al. | |
| 6,287,791 B1 | 9/2001 | Terstappen et al. | |
| 6,307,372 B1 | 10/2001 | Sugarman et al. | 324/321 |
| 6,326,787 B1 | 12/2001 | Cowgill | 324/318 |
| 6,361,749 B1 | 3/2002 | Terstappen et al. | |
| 6,361,944 B1 | 3/2002 | Mirkin et al. | 435/6.11 |
| 6,365,362 B1 | 4/2002 | Terstappen et al. | |
| 6,396,274 B1 * | 5/2002 | Commens et al. | 324/321 |
| 6,397,094 B1 | 5/2002 | Ludeke et al. | 600/411 |
| 6,404,193 B1 | 6/2002 | Dourdeville | |
| 6,456,072 B1 | 9/2002 | Webb et al. | 324/308 |
| 6,469,636 B1 | 10/2002 | Baird et al. | |
| 6,487,437 B1 | 11/2002 | Viswanathan et al. | 600/423 |
| 6,512,941 B1 | 1/2003 | Weiss et al. | 600/410 |
| 6,514,415 B2 | 2/2003 | Hatch et al. | |
| 6,551,843 B1 | 4/2003 | Rao et al. | |
| 6,555,324 B1 | 4/2003 | Olweus et al. | |
| 6,587,706 B1 | 7/2003 | Viswanathan | 600/410 |
| 6,594,517 B1 | 7/2003 | Nevo | 600/411 |
| 6,620,627 B1 | 9/2003 | Liberti et al. | |
| 6,623,982 B1 | 9/2003 | Liberti et al. | |
| 6,623,983 B1 | 9/2003 | Terstappen et al. | |
| 6,645,731 B2 | 11/2003 | Terstappen et al. | |
| 6,660,159 B1 | 12/2003 | Terstappen et al. | |
| 6,696,838 B2 | 2/2004 | Raftery et al. | 324/321 |
| 6,700,379 B2 | 3/2004 | Peck et al. | |
| 6,788,061 B1 | 9/2004 | Sweedler et al. | 324/321 |
| 6,790,366 B2 | 9/2004 | Terstappen et al. | |
| 6,822,454 B2 | 11/2004 | Peck et al. | 324/321 |
| 6,845,262 B2 | 1/2005 | Albert et al. | 608/420 |
| 6,858,384 B2 | 2/2005 | Terstappen et al. | |
| 6,876,200 B2 | 4/2005 | Anderson et al. | |
| 6,890,426 B2 | 5/2005 | Terstappen et al. | |
| 6,898,430 B1 | 5/2005 | Liberti et al. | |
| 6,914,538 B2 | 7/2005 | Baird et al. | |
| 6,958,609 B2 | 10/2005 | Raftery et al. | 324/321 |
| 7,011,794 B2 | 3/2006 | Kagan et al. | |
| 7,056,657 B2 | 6/2006 | Terstappen et al. | |
| 7,078,224 B1 | 7/2006 | Bitner et al. | |
| 7,096,057 B2 | 8/2006 | Hockett et al. | |
| 7,141,978 B2 | 11/2006 | Peck et al. | 324/321 |
| 7,164,123 B2 * | 1/2007 | Morris et al. | 250/287 |
| 7,200,430 B2 | 4/2007 | Thomas et al. | |
| 7,202,667 B2 | 4/2007 | Barbic | 324/318 |
| 7,268,552 B1 * | 9/2007 | Gerald et al. | 324/318 |
| 7,271,592 B1 | 9/2007 | Gerald, II et al. | 324/321 |
| 7,274,191 B2 | 9/2007 | Park et al. | 324/318 |
| 7,282,180 B2 | 10/2007 | Tibbe et al. | |
| 7,282,350 B2 | 10/2007 | Rao et al. | |
| 7,304,478 B2 | 12/2007 | Tsuda et al. | |
| 7,332,288 B2 | 2/2008 | Terstappen et al. | |
| 7,345,479 B2 | 3/2008 | Park et al. | 324/300 |
| 7,403,008 B2 | 7/2008 | Blank et al. | 324/316 |
| 7,405,567 B2 | 7/2008 | McDowell | 324/318 |
| 7,564,245 B2 | 7/2009 | Lee | 324/321 |
| 7,666,308 B2 | 2/2010 | Scholtens et al. | |
| 7,687,269 B2 * | 3/2010 | Kautz et al. | 436/52 |
| 7,688,777 B2 | 3/2010 | Liberti, Jr. et al. | |
| 7,764,821 B2 | 7/2010 | Coumans et al. | |
| 7,815,863 B2 | 10/2010 | Kagan et al. | |
| 7,828,968 B2 | 11/2010 | Tibbe et al. | |
| 7,863,012 B2 | 1/2011 | Rao et al. | |
| 7,901,950 B2 | 3/2011 | Connelly et al. | |
| 7,943,397 B2 | 5/2011 | Tibbe et al. | |
| 8,102,176 B2 | 1/2012 | Lee | |
| 8,110,101 B2 | 2/2012 | Tibbe et al. | |
| 8,111,669 B2 | 2/2012 | Liberti, Jr. et al. | |
| 8,128,890 B2 | 3/2012 | Droog et al. | |
| 2001/0018192 A1 | 8/2001 | Terstappen et al. | |
| 2002/0009759 A1 | 1/2002 | Terstappen et al. | |
| 2002/0012669 A1 | 1/2002 | Presnell et al. | |
| 2002/0098531 A1 | 7/2002 | Thacker | |
| 2002/0130661 A1 | 9/2002 | Raftery et al. | 324/318 |
| 2002/0132228 A1 | 9/2002 | Terstappen et al. | |
| 2002/0141913 A1 | 10/2002 | Terstappen et al. | |
| 2002/0149369 A1 * | 10/2002 | Peck et al. | 324/321 |
| 2002/0164659 A1 | 11/2002 | Rao et al. | |
| 2002/0172987 A1 | 11/2002 | Terstappen et al. | |
| 2003/0003441 A1 | 1/2003 | Colston et al. | |
| 2003/0088181 A1 | 5/2003 | Gleich | 600/434 |
| 2003/0092029 A1 | 5/2003 | Josephson et al. | 435/6.12 |
| 2003/0129676 A1 | 7/2003 | Terstappen et al. | |
| 2003/0203507 A1 | 10/2003 | Liberti et al. | |

(56) References Cited

U.S. PATENT DOCUMENTS

| | | |
|---|---|---|
| 2003/0206577 A1 | 11/2003 | Liberti et al. |
| 2003/0222648 A1 | 12/2003 | Fan .................. 324/318 |
| 2004/0004043 A1 | 1/2004 | Terstappen et al. |
| 2004/0018611 A1 | 1/2004 | Ward et al. .......... 435/287.2 |
| 2004/0072269 A1 | 4/2004 | Rao et al. |
| 2004/0076990 A1 | 4/2004 | Picard et al. |
| 2004/0101443 A1 | 5/2004 | Kagan et al. |
| 2004/0118757 A1 | 6/2004 | Terstappen et al. |
| 2005/0003464 A1 | 1/2005 | Tibbe et al. |
| 2005/0026144 A1 | 2/2005 | Maes et al. |
| 2005/0030033 A1* | 2/2005 | Peck et al. ............ 324/321 |
| 2005/0043521 A1 | 2/2005 | Terstappen et al. |
| 2005/0111414 A1 | 5/2005 | Liberti et al. |
| 2005/0128985 A1 | 6/2005 | Liberti et al. |
| 2005/0181353 A1 | 8/2005 | Rao et al. |
| 2005/0181463 A1 | 8/2005 | Rao et al. |
| 2005/0245814 A1 | 11/2005 | Anderson et al. ......... 600/410 |
| 2005/0253587 A1* | 11/2005 | Peck et al. ............ 324/321 |
| 2006/0024756 A1 | 2/2006 | Tibbe et al. |
| 2006/0115380 A1 | 6/2006 | Kagan et al. |
| 2006/0129327 A1 | 6/2006 | Kim et al. |
| 2006/0147901 A1 | 7/2006 | Jan et al. |
| 2006/0164085 A1* | 7/2006 | Morris et al. ............ 324/321 |
| 2006/0194192 A1 | 8/2006 | Rao et al. |
| 2006/0257847 A1 | 11/2006 | Scholtens et al. |
| 2006/0281094 A1 | 12/2006 | Squirrell et al. |
| 2007/0037173 A1 | 2/2007 | Allard et al. |
| 2007/0090836 A1 | 4/2007 | Xiang et al. |
| 2007/0114181 A1 | 5/2007 | Li et al. |
| 2007/0116602 A1 | 5/2007 | Lee ................ 422/82.01 |
| 2007/0117158 A1 | 5/2007 | Coumans et al. |
| 2007/0117212 A1* | 5/2007 | Kautz et al. ............ 436/137 |
| 2007/0152669 A1 | 7/2007 | Park et al. ............ 324/321 |
| 2007/0152670 A1 | 7/2007 | Park et al. ............ 324/321 |
| 2007/0154960 A1 | 7/2007 | Connelly et al. |
| 2007/0296413 A1 | 12/2007 | Park et al. |
| 2008/0042650 A1 | 2/2008 | McDowell |
| 2008/0113350 A1 | 5/2008 | Terstappen |
| 2008/0204022 A1 | 8/2008 | Sillerud et al. ............ 324/318 |
| 2008/0272788 A1 | 11/2008 | McDowell ............ 324/318 |
| 2008/0315875 A1 | 12/2008 | Sillerud ............ 324/307 |
| 2009/0061456 A1 | 3/2009 | Allard et al. |
| 2009/0061476 A1 | 3/2009 | Tibbe et al. |
| 2009/0061477 A1 | 3/2009 | Tibbe et al. |
| 2009/0134869 A1 | 5/2009 | Lee |
| 2009/0136946 A1 | 5/2009 | Connelly et al. |
| 2009/0146658 A1 | 6/2009 | McDowell et al. ............ 324/309 |
| 2009/0173681 A1 | 7/2009 | Siddiqi |
| 2009/0191535 A1 | 7/2009 | Connelly et al. |
| 2009/0256572 A1 | 10/2009 | McDowell |
| 2009/0258365 A1 | 10/2009 | Terstappen et al. |
| 2009/0286264 A1 | 11/2009 | Scholtens et al. |
| 2010/0072994 A1 | 3/2010 | Lee et al. |
| 2010/0141255 A1* | 6/2010 | Adolphi et al. ............ 324/309 |
| 2010/0282788 A1 | 11/2010 | Liberti |
| 2010/0326587 A1 | 12/2010 | Kagan et al. |
| 2011/0014686 A1 | 1/2011 | Tibbe et al. |
| 2011/0018538 A1 | 1/2011 | Lee |
| 2011/0044527 A1 | 2/2011 | Tibbe et al. |
| 2011/0046475 A1 | 2/2011 | Assif et al. |
| 2011/0052037 A1 | 3/2011 | Coumans et al. |
| 2011/0059444 A1 | 3/2011 | Stromberg et al. |
| 2011/0070586 A1 | 3/2011 | Slezak et al. |
| 2011/0091987 A1 | 4/2011 | Weissleder et al. |
| 2011/0104718 A1 | 5/2011 | Rao et al. |
| 2011/0183398 A1 | 7/2011 | Dasaratha et al. |
| 2011/0262893 A1 | 10/2011 | Dryga et al. |
| 2011/0300551 A1 | 12/2011 | Rao et al. |
| 2012/0094275 A1 | 4/2012 | Rao et al. |

FOREIGN PATENT DOCUMENTS

| | | |
|---|---|---|
| WO | 89/06699 A1 | 7/1989 |
| WO | 90/08841 A1 | 8/1990 |
| WO | 91/02811 A1 | 3/1991 |
| WO | 92/08805 A1 | 5/1992 |
| WO | 92/15883 A1 | 9/1992 |
| WO | WO 01/73460 A1 | 10/2001 |
| WO | WO 02/098364 | 12/2002 |
| WO | WO 2005/026762 | 3/2005 |
| WO | WO 2008/119054 | 10/2008 |
| WO | 2009/048673 A2 | 4/2009 |
| WO | 2011/133630 A1 | 10/2011 |
| WO | 2011/133632 A1 | 10/2011 |
| WO | 2011/133759 A1 | 10/2011 |
| WO | 2011/133760 A1 | 10/2011 |

OTHER PUBLICATIONS

Armenean et al., "NMR Radiofrequency Microcoil Design: Electromagnetic Simulation Usefulness," *Compes Rendus—Biologies*, Elsevier, Paris, vol. 325, No. 4, Apr. 1,2002, pp. 457-463.

Armenean et al., "Solenoidal and Planar Microcoils for NMR Spectroscopy," *Proceedings of the 25th Annual International Conference of the IEEE Engineering in Medicine and Biology Society*, Cancun, Mexico, Sep. 17, 2003, pp. 3045-3048.

Fukushima, et al., "Experimental Pulse NMR; A Nutes and Bolts Approach," *Addison-Wesley Publ. Co., MA*, 1981, pp. 311, 342, 374.

Goloshevsky, A.G., et al. "Development of Low Field Nuclear Magnetic Resonance Microcoils," *Rev. Sci. Inst.*, vol, 76, 2005, pp. 024101-1 through 024101-6.

Hoult et al., "The Signal-to-Noise Ratio of the Nuclear Magnetic Resonance Experiment," *J. Magn. Reson.*, vol. 24,1976, pp. 71-85.

Kaittanis et al., One-Step, Nanoparticle-Mediated Bacterial Detection with Magnetic Relaxation,: Nano Letters, vol. 7, No. 2, 2007, pp. 381-383.

Lee et al., "Chip-NRM Biosensor for Detection and Molecular Analysis of Cells," Nature Medicine, vol. 14, No. 8, Aug. 2008, pp. 869-874.

Magin et al., "Miniature Magnetic Resonance Machines," *IEEE Spectrum*, IEEE Inc. New York, vol. 34, No. 10, Oct. 1, 1997, pp. 51-61.

Massin et al., "Planar Microcoil-Based Magnetic Resonance Imaging of Cells," *Transducers '03, The 12th International Conference on Soild State Sensors, Actuators and Microsystems*, Boston, Jun. 8-12, 2003, pp. 967-970.

McDowell et al., "Low-Field Micro-Coil Probe Development for Portable NMR," 8th ICMRM, The Heidelberg Conference, Mibu, Japan, Aug. 22-26, 2005, 14 pages. (pp. 2-14 are a magnification of p. 1).

McDowell et al., "Low-Field Micro-Coil Probe Development for Portable NMR," 8th ICMRM, The Heidelberg Conference, Mibu, Japan, Conference Program Abstract, Aug. 22-26, 2005, 1 page.

McDowell et al., "Operating Nanoliter Scale NMR Microcoils in a Itesla Field," Journal of Magnetic Resonance, Academic Press, Orlando, Florida, vol. 188, No. 1, Sep. 1, 2007, pp. 74-82.

Minard et al., "Solenoidal Microcoil Design, Part 1: Optimizing rf Homogeneity," *Concepts in Magn. Reson.*, vol. 13, 2001, pp. 128-142.

Moresi, G., et al., Miniature Permanent Magnet for Table-Top NMR, *Concept. Magn. Reson.*, V. 19B, 2003, pp. 35-43.

Pappas et al., "Cellular Separations: A Review of New Challenges in Analytical Chemistry," Analytica Chemica Acta, 601, 2007.

Peck et al., "Design and Analysis of Microcoils for NMR Microscopy," *J. Magn. Reson.*, vol. 108, 1995, pp, 114-124.

Peck et al., "RF Microcoils Patterned Using Microlithographic Techniques for Use as Microsensors in NMR," *Engineering in Medicine and Biology Society*, Proceedings of the 15th Annual International Conference of the IEEE Oct. 28-31, 1993, pp. 174-175.

Seeber et al., "Design and Testing of High Sensitivity Microreceiver Coil Apparatus for Nuclear Magnetic Resonance and Imagin," *Rev. Sci. Inst.*, vol. 72, 2001, p. 2171-2179.

Seeber et al., "Triaxial Magnetic Field Gradient System for Microcoil Magnetic Resonance Imaging," *Review of Scientific Instruments*, vol. 71, No. 11, Nov. 2000, pp. 4263-4272.

(56) References Cited

OTHER PUBLICATIONS

Sillerud et al., "1 H NMR Detection or Superparamagnetic Nanoparticles at 1T Using a Microcoil and Novel Tuning Circuit," *Journal of Magnetic Resonance, Academic Press*, Orland, Florida, Aug. 1, 2006, pp. 181-190.
Sorli et al., "Micro-Spectrometer for NMR: Analysis of Small Quantities in Vitro," *Mes. Sci. Technol.*, vol. 15, 2004, pp. 877-880.
Subramanian et al., "RF Microcoil Design for Practical NMR of Mass-Limited Samples,"*Journal of Magnetic Resonance*, Academic Press, Orlando, Florida, vol. 133, No, 1, Jul. 1, 1998, pp. 227-231.
Taktak et al., Multiparameter Magnetic Relaxation Switch Assays, Analytical Chemistry, vol. 79, No. 23, Dec. 1, 2007, pp. 8863-8869.
Van Bentum et al., "Towards Nuclear Magnetic Resonance µ-Spectroscopy and µ—Imaging," *Analyst, Royal Society of Chemistry*, London, vol. 129, No. 9, Jan. 1, 2004, pp. 793-803.
Notification of Transmittal of the International Search Report and the Written Opinion of the International Searching Authority, or the Declaration for International Application No. PCT/US2009/067577 mailed Feb. 5, 2010, 13 pages.
Listing of Claims for International Application No. PCT/US2009/067577 filed Dec. 10, 2009, 14 pages.
Peck et al., Design and Analysis of Microcoils for NMR Microscopy, *J. Magan. Reson.* B108 (1995), pp. 114-124.
Behnia and Webb, Limited-Sample NMR Using Solenoidal Microcoils, Perfluorocarbon Plugs, and Capillary Spinning, Anal. Chem., 70:5326-5331 (1998).
Byrne, et al., Antibody-Based Sensors: Principles, Problems and Potential for Detection of Pathogens and Associated Toxins, Sensors, 9:4407-4445 (2009).
Chapman, et al., Use of commercial enzyme immunoassays and immunomagnetic separation systems for detecting *Escherichia coli* O157 in bovine fecal samples, Applied and Environmental Microbiology, 63(7):2549-2553 (1997).
Ciobanu and Pennington, 3D Micron-scale MRI of Single Biological Cells, Solid State Nucl. Magn. Reson., 25:138-141 (2004).
Cross, et al., Choice of Bacteria in Animal Models of Sepsis, Infec. Immun. 61(7):2741-2747 (1983).
Djukovic, et al., Signal Enhancement in HPLC/Microcoil NMR Using Automated Column Trapping, Anal. Chem., 78:7154-7160 (2006).
Drancourt, et al., Diagnosis of Mediterranean Spotted Fever by Indirect Immunofluorescence of Rickettsia conorii in Circulating Endothelial Cells Isolated with Monoclonal Antibody-Coated Immunomagnetic Beads, J. Infectious Diseases, 166(3):660-663, 1992.
Fan, et al., Self-assembly of ordered, robust, three-dimensional gold nanocrystal/silica arrays, Science, 304:567 (2004).
Fu, et al., Rapid Detection of *Escherichia coli* O157:H-7 by Immunogmagnetic Separation and Real-time PCR, Int. J. Food Microbiology, 99(1):47-57, (2005).
Goding, J.W., Conjugation of antibodies with fluorochromes: modifications to the standard methods, J. Immunol. Meth., 13:215 (1976).
Goloshevsky, et al., Integration of Biaxial Planar Gradient Coils and an RF Microcoil for NMR Flow Imaging, Meas. Sci. Technol., 16:505-512 (2005).
Grant, et al., Analysis of Multilayer Radio Frequency Microcoils for Nuclear Magnetic Resonance Spectroscopy, IEEE Trans. Magn., 37:2989-2998 (2001).
Grant, et al., NMR Spectroscopy of Single Neurons, Magn. Reson. Med., 44:19-22 (2000).
Halbach, Design of Permanent Multipole Magnets with Oriented Rare Earth Cobalt Material, Nuclear Instrum Methods, 169:1-10 (1980).
Harada, et al., Monoclonal antibody G6K12 specific for membrane-associated differentiation marker of human stratified squamous epithelia and squamous cell carcinoma, J. Oral. Pathol. Med., 22(4):1145-152 (1993).
Hijmans, et al., An immunofluorescence procedure for the detection of intracellular immunoglobulins, Clin. Exp. Immunol., 4:457 (1969).

Hirsch, et al., Easily reversible desthiobiotin binding to streptavidin, avidin, and other biotin-binding proteins: uses for protein labeling, detection, and isolation, Anal. Biochem., 208(2):343-57 (2002).
Inai, et al., Immunohistochemical detection of an enamel protein-related epitope in rat bone at an early stage of osteogenesis, Histochemistry, 99(5):335-362 (1993).
Engvall, Enzyme immunoassay ELISA and EMIT, Meth. in Enzymol., 70:419-439 (1980).
International Search Report in PCT/US2011/33184, mailed Jul. 25, 2011, 2 pages.
International Search Report in PCT/US2011/33186, mailed Jun. 22, 2011, 1 page.
ISR and Written Opinion in PCT/US2011/48447, mailed Dec. 22, 2011, 7 pages.
ISR and Written Opinion in PCT/US2011/48452, mailed Dec. 22, 2011, 7 pages.
International Search Report in PCT/US2011/33411, mailed Jun. 22, 2011, 3 page.
International Search Report in PCT/US2011/33410, mailed Jul. 19, 2011, 2 pages.
Johne, et al., *Staphylococcus aureus* exopolysaccharide in vivo demonstrated by immunomagnetic separation and electron microscopy, J. Clin. Microbiol. 27:1631-1635 (1989).
Johnson, Thermal Agitation of Electricity in Conductors, Phys. Rev., 32:97-109 (1928).
Lund, et al., Immunomagnetic separation and DNA hybridization for detection of enterotoxigenic *Escherichia coli* in a piglet model, J. Clin. Microbiol., 29:2259-2262 (1991).
Malba, et al., Laser-lathe Lithography—A Novel Method for Manufacturing Nuclear Magnetic Resonance Microcoils, Biomed. Microdev., 5:21-27 (2003).
Massin, et al., Planar Microcoil-based Microfluidic NMR Probes, J. Magn. Reson., 164:242-255 (2003).
Mulder, et al., Characterization of two human monoclonal antibodies reactive with HLA-B12 and HLA-B60, respectively, raised by in vitro secondary immunization of peripheral blood lymphocytes, Hum. Immunol., 36 (3):186-192 (1993).
Nyquist, Thermal Agitation of Electrical Charge in Conductors, Phys. Rev., 32:110-113 (1928).
Olsen, et al., High resolution microcoil 1H-NMR for mass-limited, nanoliter-volume samples, Science, 270:1967 (1995).
Olson, et al., High-resolution microcoil NMR for analysis of mass-limited, nanoliter samples, Anal. Chem., 70:645-650 (1998).
Perez, et al., Viral-induced self-assembly of magnetic nanoparticle allows detection of viral particles in biological media, J. Am. Chem. Soc., 125:10192-10193 (2003).
Qiu, et al., Immunomagnetic separation and rapid detection of bacteria using bioluminescence and microfluidics, Talanta, 79:787-795 (2009).
Rogers, et al., Using microcontact printing to fabricate microcoils on capillaries for high resolution proton nuclear magnetic resonance on nanoliter volumes, Appl. Phys. Lett., 70:2464-2466 (1997).
Skjerve, et al., Detection of Listeria monocytogenes in foods by immunomagnetic separation, Appl. Env. Microbiol., 56:3478 (1990).
Stauber, et al., Rapid generation of monoclonal antibody-secreting hybridomas against African horse sickness virus by in vitro immunization and the fusion/cloning technique, J. Immunol. Methods, 161(2):157-168 (1993).
Stocker, et al., Nanoliter volume, high-resolution NMR Microspectroscopy using a 60 um planer microcoil, IEEE Trans. Biomed. Eng., 44:1122-1127 (1997).
Torensama, et al., Monoclonal Antibodies Specific for the Phase-Variant O-Acetylated Ki Capsule of *Escerichia coli*, J. Clin. Microbiol., 29(7):1356-1358 (1991).
Trumbull, et al., Integrating microfabricated fluidic systems and NMR spectroscopy, IEEE Trans. Biomed. Eng., 47 (1):3-7 (2000).
Venkateswaran, et al., Production of Anti-Fibroblast Growth Factor Receptor Monoclonal Antibodies by In Vitro Immunization, Hybridoma, 11(6):729-739 (1992).

(56) References Cited

OTHER PUBLICATIONS

Vermunt, et al., Isolation of salmonelas by immunomagnetic separation, J. Appl. Bact., 72:112-118 (1992).

Wang and Irudayaraj, Multifunctional Magnetic-Optical Nanoparticle Probes for Simultaneous Detection, Separation, and Thermal Ablation of Multiple Pathogens, Small, 6(2):283-289 (2010).

Webb and Grant, Signal-to-Noise and Magnetic Susceptibility Tradeoffs in Solenoidal Microcoils for NMR, J. Magn. Reson. B, 113:83-87 (1996).

Wensink, et al., High Signal to Noise Ratio in Low-field NMR on a Chip: Simulations and Experimental Results, 17th IEEE MEMS, 407-410 (2004).

Williams and Wang, Microfabrication of an electromagnetic power micro-relay using SU-8 based UV-LIGA technology, Microsystem Technologies, 10(10):699-705 (2004).

Wu, et al., 1H-NMR Spectroscopy on the Nanoliter Scale for Static and On-Line Measurements, Anal. Chem., 66:3849 (1994).

Zhao, et al., A rapid bioassay for single bacterial cell quantitation using bioconjugated nanoparticles, PNAS, 101 (42):15027-15032 (2004).

* cited by examiner

NMR, INSTRUMENTATION, AND FLOW METER/CONTROLLER CONTINUOUSLY DETECTING MR SIGNALS, FROM CONTINUOUSLY FLOWING SAMPLE MATERIAL

CROSS-REFERENCE TO RELATED APPLICATIONS

This application claims the benefit of U.S. Provisional Application No. 61/121,416 of Adolphi et al., filed on Dec. 10, 2008.

BACKGROUND

The phenomenon of nuclear magnetic resonance (NMR) has been used as an analytical tool in science and medicine for some time. Generally speaking, NMR is sensitive to a wide range of chemical and physical properties of objects of analytical study, such as animate and inanimate subjects, and may be made sensitive to spatial position of such objects as well. As such, NMR technology, such as NMR principles, methods, and/or apparatus, may be used in a variety of applications. By way of example, an NMR apparatus may be used in an analytical chemistry application, in which the apparatus may be used to determine the chemical composition of a sample material. Further by way of example, an NMR apparatus may be used in a medical imaging application, in which the apparatus, such as a magnetic resonance imaging (MRI) scanner, for example, may be used to view structures inside an intact human. Still further by way of example, NMR technology may be useful for studying any of a variety of or combination of properties, such as the structure of a solid or a semi-solid, temperature, pressure, elasticity, velocity, and/or any of other static or dynamic physical properties. Data from NMR studies, such as that concerning chemical and/or physical properties of an object of study, may be integrated together and/or integrated with data from MRI studies. A "functional MRI" study of localized brain activity is merely one example of such an integration of data.

Generally, functional roles of various components of different NMR apparatus have been developed to varying degrees. In the case of an NMR spectrometer, for example, such roles have been fairly well established. In most NMR technology, a source of magnetic field is used to bring about the NMR phenomenon. The source may be a superconducting electromagnet (such as that often used in modern NMR and MRI instruments), non-superconducting electromagnets, such as iron-core and/or air-core electromagnets, for example, or permanent magnets. An NMR magnet generally has a region over which its field, or the intensity thereof, is substantially uniform or homogeneous, such as at least 100 parts per million (ppm) for a magnet used in an MRI application and perhaps as high as 1 part per billion (ppb) for a magnet used in an analytical chemistry NMR application, by way of example. Lower degrees of uniformity or homogeneity can often be adequate for useful measurement in various applications. A single coil or microcoil (see, for example, T. L. Peck, et al., *Design and Analysis of Microcoils for NMR Microscopy*, J. Magn. Reson. B108 (1995), pp. 114-124) may be placed inside the region of the substantially homogeneous field and the object or sample of study, such as a sample material sample, for example, may be held inside the coil. The coil may be a solenoid, a saddle-coil, a surface coil, or any other structure capable of coupling to the sample magnetically. While some coils are helical in shape, a useful coil may be helical or non-helical in shape.

Various suitable NMR electronic components, such as transmit and receive circuitry (which may be combined into a single "transceiver" unit), for example, may be coupled to the coil to excite magnetic resonance in the sample and to detect a signal, such as a voltage signal, for example, that the magnetic resonance in the sample creates in the coil. The excitation input may be radio-frequency (rf) energy or power, such as a short burst or a series of pulses of rf energy or power, the duration of which may be many orders of magnitude shorter than the duration of the magnetic resonance signal coming from the sample. The transmit and receive circuitry may include various functional components, such as any of a variety of components suitable for modifying or processing the excitation input or modifying or processing (such as amplifying, for example) the signal from the sample. By way of example, an NMR spectrometer may have hardware and/or software components suitable for manipulation of the signal to provide an output meaningful to the recipient of the output, such as a human operator. Further by way of example, an MRI scanner may have components suitable for providing spatial information that is useful for forming images. An NMR apparatus, such as an MRI scantier, for example, may employ more than one independent coil surrounding the sample, wherein one coil is used to excite magnetic resonance in the sample and another coil is used to detect magnetic resonance from the sample. In such a case, the excitation coil may be coupled to transmit circuitry and the detection may be coupled to the receive circuitry of the electronic system employed.

While the functioning of various components of different NMR apparatus have been developed to varying degrees, such as generally described above, the technology used to achieve such roles or such functioning continues to evolve. Development of NMR technology, such as apparatus, applications, methods, and/or the like, is generally desirable.

SUMMARY

NMR technology disclosed herein, such as an NMR apparatus or method, for example, described herein may be useful for purposes described herein, such as determining presence or absence of magnetic resonance from a sample, for example. Methods pertaining to such NMR technology include methods of designing or constructing NMR apparatus, methods of using NMR apparatus, methods of employing data obtained from NMR apparatus, and/or the like. A summary of various aspects, features, embodiments, and examples, pertaining to such technology, is provided herein.

Various apparatus for detection of magnetic resonance in sample material are disclosed herein. Merely by way of example, sample material may be arranged relative to such an apparatus such that it comprises a first region that is located upstream relative to a second region. The apparatus may comprise any of a variety of suitable elements, such as at least one source of magnetic field. That source may be that sufficient to provide a substantially uniform magnetic field over a magnetic field region. The magnetic field region may comprise at least the first region and the second region associated with the sample material. The sample material may take a variety of forms as further described herein. If the sample material is relatively self-contained, as in the case of many a solid sample material, for example, the apparatus may be such that it does or does not comprise a containment vehicle. Accordingly, the sample may or may not comprise a containment vehicle, such as one of a construction sufficient for containing the sample material. In the former case, the containment vehicle may comprise at least a first region that is located upstream relative to a second region.

Any one or both of the first region and the second region of the sample and/or the containment vehicle may be useful as for excitation, detection, and/or excitation/detection. As such, a region may be referred to as an excitation region, a detection region, and/or an excitation/detection region, as further described herein.

The apparatus may comprise at least one first coil disposed within the magnetic field region and in a vicinity of the first region. The at least one first coil may be sufficient for excitation of sample material in the first region to magnetic resonance via excitation energy. The apparatus may comprise at least one second coil disposed within the magnetic field region and in a vicinity of the second region. The at least one second coil may be sufficient for detection of magnetic resonance in sample material in the second region.

The apparatus may comprise at least one transmitter operably or electrically coupled to the at least one first coil. The at least one transmitter may be sufficient to transmit excitation energy to the at least one first coil. The apparatus may comprise at least one receiver operably or electrically coupled to the at least one second coil. The at least one receiver may be sufficient to receive at least one magnetic resonance signal from the at least one second coil.

An apparatus such as that described above may be amenable for use in a detection method. A method for detection of magnetic resonance in sample material may comprise any of a variety of suitable elements. Merely by way of example, such a method may comprise providing sample material to such an apparatus or other suitable apparatus, providing a substantially uniform magnetic field over the magnetic field region, transmitting excitation energy to the at least one first coil, receiving at least one magnetic resonance signal, and/or any suitable combination thereof.

An apparatus for detection of magnetic resonance in sample material may comprise any of various of the above-mentioned features and/or elements, such as any of those concerning sample material, a possible containment vehicle, and/or at least one source of magnetic field. Such an apparatus may comprise any of a variety of suitable elements, such as at least one first excitation/detection coil disposed within the magnetic field region and in a vicinity of a first region. The at least one first coil may be sufficient for excitation of sample material in the first region to magnetic resonance via excitation energy and for detection of magnetic resonance in sample material in the first region. Such an apparatus may comprise at least one second excitation/detection coil disposed within the magnetic field region and in a vicinity of the second region. The at least one second coil may be sufficient for excitation of sample material in the second region to magnetic resonance via excitation energy and for detection of magnetic resonance in sample material in the second region.

Such an apparatus may comprise at least one first transmitter/receiver operably or electrically coupled to the at least one first excitation/detection coil. The at least one first transmitter/receiver may be sufficient to transmit excitation energy to the at least one first excitation/detection coil and to receive at least one magnetic resonance signal from the at least one first excitation/detection coil.

Such an apparatus may comprise at least one second transmitter/receiver operably or electrically coupled to the at least one second excitation/detection coil. The at least one second transmitter/receiver may be sufficient to transmit excitation energy to the at least one second excitation/detection coil and to receive at least one magnetic resonance signal from the at least one second excitation/detection coil.

An apparatus such as that described above may be amenable for use in a detection method. A method for detection of magnetic resonance in sample material may comprise any of a variety of suitable elements. Merely by way of example, such a method may comprise providing sample material to such an apparatus or other suitable apparatus, providing a substantially uniform magnetic field over the magnetic field region, transmitting excitation energy to the at least one first excitation/detection coil and excitation energy to the at least one second excitation/detection coil, receiving at least one magnetic resonance signal from the at least one first excitation/detection coil and at least one magnetic resonance signal from the at least one second excitation/detection coil, and/or any suitable combination thereof.

An apparatus for detection of magnetic resonance in sample material may comprise various of the above-mentioned features and/or elements, such as any of those concerning sample material, a possible containment vehicle, and/or at least one source of magnetic field. Such an apparatus may comprise any of a variety of suitable elements, such as at least one first excitation/detection coil disposed within the magnetic field region and in a vicinity of the first region. The at least one first coil may be sufficient for excitation of sample material in the first region to magnetic resonance via excitation energy and for detection of magnetic resonance in sample material in the first region. Such an apparatus may comprise at least one second excitation/detection coil disposed within the magnetic field region and in a vicinity of the second region. The at least one second coil may be sufficient for excitation of sample material in the second region to magnetic resonance via excitation energy and for detection of magnetic resonance in sample material in the second region. In such an apparatus, the at least one first excitation/detection coil and the at least one second excitation/detection coil may be operably or electrically coupled.

Such an apparatus may comprise at least one transmitter/receiver operably or electrically coupled to the at least one first excitation/detection coil and the at least one second excitation/detection coil. The at least one transmitter/receiver may be sufficient to transmit excitation energy to the at least one first excitation/detection coil and the at least one second excitation/detection coil, and may be sufficient to receive at least one magnetic resonance signal from the at least one first excitation/detection coil and the at least one second excitation/detection coil.

An apparatus such as that described above may be amenable for use in a detection method. A method for detection of magnetic resonance in sample material may comprise any of a variety of suitable elements. Merely by way of example, such a method may comprise providing sample material to such an apparatus or other suitable apparatus, providing a substantially uniform magnetic field over the magnetic field region, transmitting excitation energy to the at least one first excitation/detection coil and to the at least one second excitation/detection coil, receiving at least one magnetic resonance signal from the at least one first excitation/detection coil and the at least one second excitation/detection coil, and/or any suitable combination thereof.

An apparatus for detection of magnetic resonance in sample material may comprise various of the above-mentioned features and/or elements, such as any of those concerning sample material, a possible containment vehicle, and/or at least one source of magnetic field. Such an apparatus may comprise any of a variety of suitable elements, such as at least one excitation coil disposed within the magnetic field region and in a vicinity of the first region and the second region. The at least one excitation coil may be sufficient for excitation of sample material in the first region and in the second region to magnetic resonance via excitation energy. Such an apparatus may comprise at least one first detection coil disposed within the magnetic field region and in a vicinity of the first region. The at least one first detection coil may be sufficient for detection of magnetic resonance in sample material in the first region.

Such an apparatus may comprise at least one second detection coil disposed within the magnetic field region and in a vicinity of the second region. The at least one second coil may be sufficient for detection of magnetic resonance in sample material in the second region. In such an apparatus, the at least one first detection coil and the at least one second detection coil may be operably or electrically coupled.

Such an apparatus may comprise at least one transmitter operably or electrically coupled to the at least one excitation coil. The at least one transmitter may be sufficient to transmit excitation energy to the at least one excitation coil. Such an apparatus may comprise at least one receiver operably or electrically coupled to the at least one first detection coil and the at least one second detection coil. The at least one receiver may be sufficient to receive sufficient to receive at least one magnetic resonance signal from the at least one first detection coil and the at least one second detection coil.

An apparatus such as that described above may be amenable for use in a detection method. A method for detection of magnetic resonance in sample material may comprise any of a variety of suitable elements. Merely by way of example, such a method may comprise providing sample material to such an apparatus or other suitable apparatus, providing a substantially uniform magnetic field over the magnetic field region, transmitting excitation energy to the at least one first coil, receiving at least one magnetic resonance signal, and/or any suitable combination thereof.

Data provided via any of the foregoing apparatus or methods may be usefully processed and/or manipulated to provide useful NMR-related information, as further described herein. In some cases, data associated with at least one data stream may be correlated in any suitable manner to provide useful information. Resulting data may be useful in that it may have good characteristics, such as low SNR, for example, and/or it may provide a good indication of a useful characteristic concerning the sample material or an object or objects therein.

These and various other aspects, features, and embodiments are further described herein. Merely by way of example, an apparatus and/or a method described herein may be useful for purposes described herein, such as determining characteristics of sample material, determining presence or absence of an object in sample material, and/or determining any of same with respect to sample material that is either stationary or in motion, for example. Any other portion of this application is incorporated by reference in this summary to the extent same may facilitate a summary of subject matter described herein, such as subject matter appearing in any claim or claims that may be associated with this application.

BRIEF DESCRIPTION OF THE DRAWINGS

A description of various aspects, features, embodiments, and/or examples is provided herein with reference to the accompanying drawings, which are briefly described below. The drawings may illustrate one or more aspect(s), feature(s), embodiment(s), and/or example(s) in whole or in part. The drawings are illustrative and are not necessarily drawn to scale.

FIG. 1a and FIG. 1b may be collectively referred to as FIG. 1.

FIG. 2a and FIG. 2b may be collectively referred to as FIG. 2.

FIG. 3a, FIG. 3b and FIG. 3c may be collectively referred to as FIG. 3.

FIG. 4a and FIG. 4b may be collectively referred to as FIG. 4.

FIG. 5a, FIG. 5b and FIG. 5c may be collectively referred to as FIG. 5.

DESCRIPTION

Figure 1A:
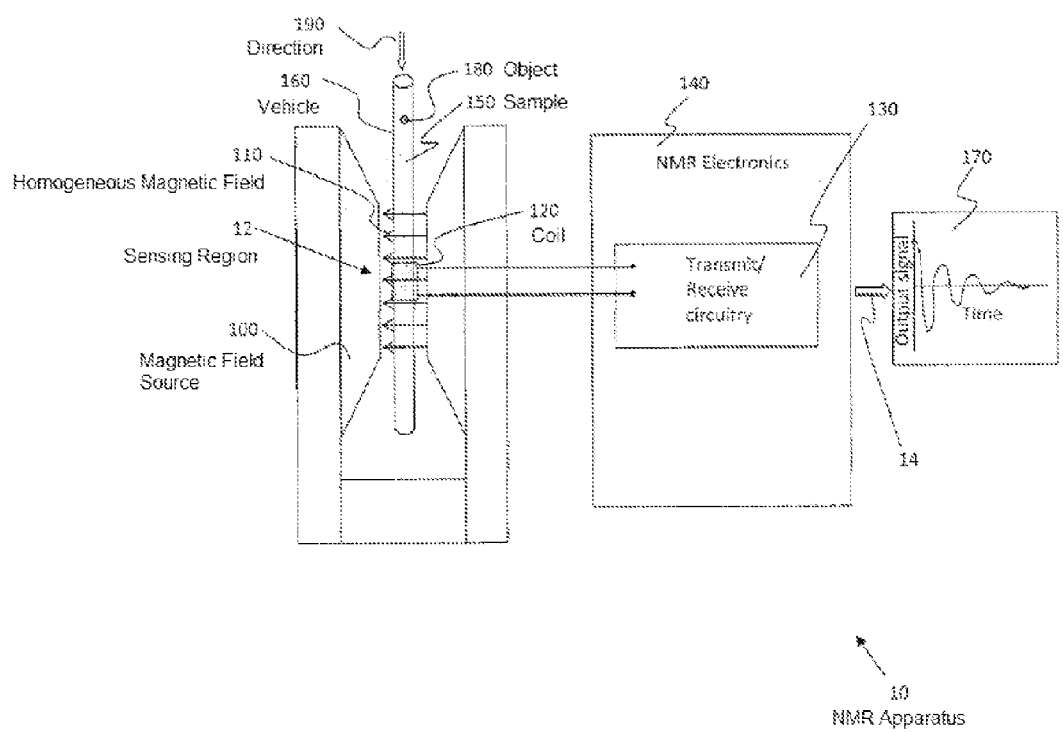
FIG. 1a is a schematic depiction of an apparatus or a device that may be used for NMR detection.

NMR technology described herein, such as an NMR apparatus or method, for example, described herein may be useful for purposes described herein, such as determining presence or absence of magnetic resonance from a sample, for example. A description of various aspects, features, embodiments, and examples, pertaining to such technology, is provided herein.

It will be understood that a word appearing herein in the singular encompasses its plural counterpart, and a word appearing herein in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives is merely illustrative, not limiting, unless implicitly or explicitly understood or stated otherwise. Still further, it will be understood that any figure or number or amount presented herein is approximate, and that any numerical range includes the minimum number and the maximum number defining the range, whether the word "inclusive" or the like is employed or not, unless implicitly or explicitly understood or stated otherwise. Yet further, it will be understood that any heading employed is by way of convenience, not by way of limitation. Additionally, it will be understood that any permissive, open, or open-ended language encompasses any relatively permissive to restrictive language, less open to closed language, or less open-ended to closed-ended language, respectively, unless implicitly or explicitly understood or stated otherwise. Merely by way of example, the word "comprising" may encompass "comprising"-, "consisting essentially of"-, and/or "consisting of"-type language.

All patents, patent applications, including provisional patent applications, such as the above-referenced U.S. Provisional Application No. 61/121,416, and non-provisional patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

Various terms may be generally described, defined, and/or used herein to facilitate understanding. It will be understood that a corresponding general description, definition, and/or use of these various terms applies to corresponding linguistic or grammatical variations or forms of these various terms. It will also be understood that a general description, definition, and/or use, or a corresponding general description, definition, and/or use, of any term herein may not apply or may not fully apply when the term is used in a non-general or more specific manner. It will also be understood that the terminology used herein, and/or the descriptions and/or definitions thereof, for the description of particular embodiments, is not limiting. It will further be understood that embodiments described herein or applications described herein, are not limiting, as such may vary.

NMR technology described herein, such as an NMR apparatus or method, for example, described herein may be useful for purposes described herein, such as determining presence or absence of magnetic resonance from a sample, such as a sample material sample, for example. By way of example, NMR analysis of sample material in flow has useful applications in medicine, chemical processing and engineering, food processing and engineering, the study of sample material flow itself, and a wide variety of other applications. NMR analysis of sample material in flow can be complicated by the fact that the flowing sample material is in transit and thus remains in the sensing region of the NMR apparatus for a limited time. The sensing region is that region of the NMR apparatus that is influenced by the excitation/detection coil or excitation and detection coils. After excitation of the sample material sample, the excited sample material provides a detectable signal in that time in which it is in the sensing region of the apparatus. In some cases, as in MRI angiography, a loss of signal attributed to flow of the sample ("washout") can be used to distinguish moving from non-moving portions of the sample. In other cases, flow of the sample may limit spectral resolution of the signal and may limit the time available for encoding spatial or other information in the NMR signal, as may be desirable for MR imaging, velocity measurements, and/or the like. In an NMR study involving a long signal acquisition period, a process, characteristic, property, or phenomena of interest may be poorly or insufficiently observable if the sample material sample is flowing at a rate that is too high. Thus, in some cases, it may be desirable to allow a sample material to flow at a rate that is at or below some threshold. An appropriate threshold for a particular NMR study may be selected based on a variety of factors, such as consideration of the process or the phenomenon under study, for example. As the threshold rate is approached, signal detection may begin to weaken, making NMR measurement more difficult.

It will be appreciated that portions of the description herein, such as those in the preceding paragraph, may refer to samples, sample materials, or to sample materials, whether stationary or flowing. It will be appreciated that each of the terms "sample" and "sample material" as used herein encompasses sample material, and the term "sample material" as used herein encompasses a material capable of movement or flow through a suitable vehicle or conduit, such as a liquid, a semi-liquid, a gel, a semi-gel, a solid, a semi-solid, a gas, and/or the like. Merely by way of example, a powder material comprising solid particles in powder form may be capable of such movement or flow. It will be appreciated that the terms "movement" and "flow" may be used interchangeably. Further, merely by way of example, a solid rod or object may be employed. A solid rod may be comprised of any suitable material for NMR analysis, such as rubber or a suitable plastic, for example. In such a case, a solid rod may be allowed to move through a suitable vehicle or conduit. Alternatively, a solid rod may act as its own vehicle or conduit in a sense, in which case it may be possible to dispense with a vehicle or conduit.

In general, a signal detected in an NMR or an MRI study may be rather weak. Such a signal may have a low signal-to-noise ratio (SNR), meaning that a randomly fluctuating (noise) portion of the detected signal may be large compared to an information-containing (signal) portion of the detected signal. A certain level of noise may be attributed to thermal fluctuation in the detector coil of the NMR apparatus; while additional noise, if any, may be attributable to the remainder of the NMR apparatus or to the sample itself. Measures may be taken to try to reduce the level of noise. Examples of such measures include careful design of the electronics used in the NMR apparatus, use of hardware and/or software filters to reduce noise in the processed data, and/or the like.

It may be difficult or impossible to remove noise entirely, such that some level of random variation or noise in data output from an NMR apparatus can be anticipated or expected. When a SNR associated with the data output is undesirably low, a technique of signal averaging may be used to try to improve the SNR and thus the data output. A simple form of signal averaging may involve repeating excitation of the coil and detection of a signal from a sample multiple times and summing the resulting signals. If the sample is the same in each repetition, such a summation may provide a better SNR, as the multiple individual signal components tend to add up, while at least some of the individual random noise components tend to at least partially cancel each other. Signal averaging may be a useful tool in a variety of applications, such as a flowing-sample material application in which the portion of the sample material in the sensing region is changing. In such a case, signal averaging may increase the SNR for that portion of the detected signal which is common to all of the repeated measurements.

An apparatus which may be used for NMR detection involving a sample material in flow is now described by way of illustration. As previously mentioned, in such an NMR detection application, it may be difficult to obtain useful data or a useful measurement, or to observe a particular process or phenomena under study, if the flowing sample material is in the sensing region of the apparatus for an undesirable, non-optimal or unsuitable amount of time. This may happen when the amount of time is unsuitably short for facilitating a sufficiently useful measurement. As also previously mentioned, while signal averaging may be used to improve or increase the SNR associated with the data or measurement obtained in such an NMR detection application, such a technique may not be sufficiently useful in a situation in which the sample material in the sensing region of the apparatus changes over the course of the multiple signal acquisitions. A reduction in the flow rate of a sample material under study may ameliorate one or more of the above-mentioned challenges, though in some cases, such a reduction in flow rate may be undesirable.

Merely by way of illustration, an apparatus and a method that may be used for NMR detection involving a sample material in a "reduced" flow or no flow state is now described in relation to FIG. 1. In this illustration, an NMR apparatus 10 is used to detect at least one object or other localized heterogeneity 180 present in a sample material sample 150 that is present in or flows through the sensing region 12 of the apparatus. It is noted that the apparatus could also be used to detect the absence of such an object or heterogeneity in the sample material. The apparatus 10 comprises a vehicle 160, such as a sample material conduit, for example, for containing the sample material sample 150 as it is either held therein, when the sample material is not in flow, or flows therethrough in direction 190 through the sensing region 12 of the apparatus.

The apparatus 10, which may be an NMR spectrometer, for example, comprises a magnetic field source 100, such as a magnet, that is sufficient to provide a substantially uniform or homogeneous magnetic field 110 in an active region which encompasses the sensing region 12 of the apparatus. As shown, the NMR apparatus comprises a single coil 120, disposed in the magnetic field 110 and placed near or surrounding the sensing region 12, which may be used for both excitation of the sample 150 and detection of a signal from the sample. The coil 120 may be operably coupled to NMR electronics 140, which may comprise transmit/receive circuitry 130 sufficient for transmission of excitation energy or power, such as rf energy, for example, to the coil 120 to excite the sample in the sensing region 12 to a state of magnetic resonance, and for reception of magnetic resonance signals, such as voltage signals, for example, from the excited sample in the sensing region.

Figure 1B:
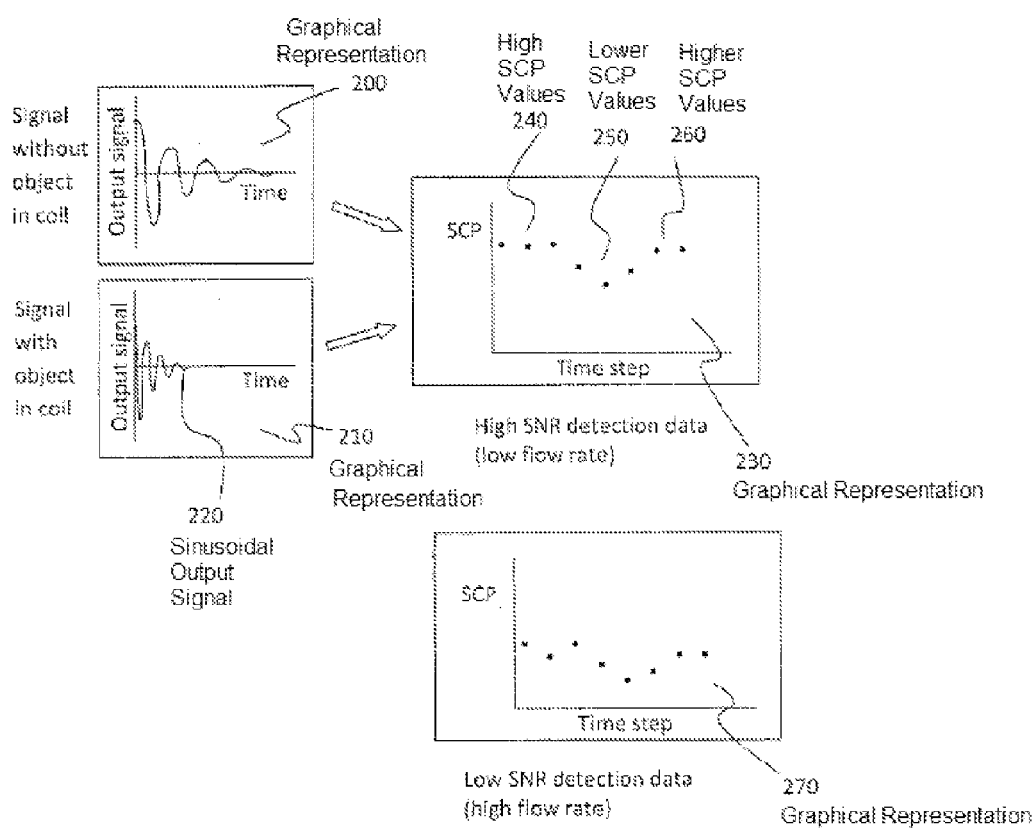
FIG. 1b shows graphical representations of output signal versus time and a signal characterization parameter versus time step corresponding to various NMR detection applications, as further described herein.

The NMR electronics 140 may comprise any suitable arrangement of components, such as any suitable arrangement or housing of components together or separately, for example. The NMR electronics 140 may comprise any components suitable for production, processing, manipulation (such as transforming, for example), communication, and/or the like, of the excitation energy, and any components suitable for the reception, processing (such as filtering, for example), manipulation (such as amplification, for example), communication, and/or the like of the detected signal. The NMR electronics 140 may comprise any software and/or hardware components suitable for manipulation of the output of the transmit/receive circuitry 130, such as that suitable for recording and/or displaying an output signal 14 in a useful format, such as a fairly simple graphical representation 170 of the output signal versus time, for example, as shown in FIG. 1a and FIG. 1b. The output signal may be presented as a decaying sinusoid, as also shown in these figures, wherein the time associated with the beginning of the sinusoid corresponds to the moment the sample material 150 is excited to magnetic resonance and the resulting magnetic resonance signal 14 lasts for a shorter or longer time as may be influenced by physical properties of, or physical processes occurring in, the excited sample material, and its time of residence in the sensing region 12. Other suitable alternative are possible. Merely by way of example, the NMR electronics 140 may comprise software and/or hardware components that are suitable for analyzing an output signal or signals to determine any of a number of features, properties, and/or characteristics thereof, such as frequency content, amplitude, signal correlation, and/or the like.

The object or heterogeneity 180 in the sample material under study may comprise a cell, a bubble, a bead, a magnetic bead, a chemical or physical impurity, a concentration of chemicals resulting from a separation apparatus such as HPLC, a different sample material, a different state within the sample material, and/or any of a wide variety of other suitable conditions for study. Generally speaking, the object 180 may be detected if its presence in the sensing region 12 causes the output signal 14 to be detectably different from an output signal 14 associated with the sample material when no object is in the sensing region 12. By way of illustration, in a situation in which the portion of a stationary sample material 150 in the sensing region 12 comprises no object 180, excitation of that portion of the sample material may produce an output signal such as that displayed in a graphical representation 200 in the upper left side of FIG. 1b. Such an output signal may be designated a background or normal or reference signal for detection associated with the sample material under study. Further by way of illustration, in a situation in which the portion of a stationary sample material 150 in the sensing region 12 comprises a stationary object 180, excitation of that portion of the sample material may produce an output signal such as that displayed in a graphical representation 210 in the lower left side of FIG. 1b. A comparison of the two graphical representations 200 and 210 produces at least one observable difference, namely, a relative shortening of the duration of the output signal 220 associated with the latter as it decays following excitation.

There are other ways to compare NMR data resulting from the situations discussed above. Merely by way of example, for each situation, the signal data can be associated with a signal characterization parameter (SCP) that has one value when there is no object present and another value when there is an object present. Any suitable SCP may be used, such as initial signal amplitude, average signal frequency, a ratio of the amplitudes of two spectral features, a ratio of signal amplitude at two different times, and/or any of a variety of other suitable characteristics. By way of illustration, the SCP may be the total "amount" of signal, or the area under the signal decay envelope. As can be seen from the graphical representations 200 and 210 described above, such an SCP value will be higher in the situation in which the portion of the stationary sample material in the sensing region comprises no object than in the situation in which the portion of a stationary sample material in the sensing region comprises a stationary object.

Any of a wide variety of factors may influence whether or not an object (or other localized heterogeneity) in a sample material will cause a measurable alteration in signal output. Merely by way of example, such factors may include a property of the object, a manner in which the object is excited, a manner in which the sample material is excited, magnetic field strength, magnetic field homogeneity, and/or the like. The NMR technology employed, such as hardware, software, process, and/or the like, may be suitably designed such that the presence (or absence) of an object produces a detectable, measurable, observable, visible, and/or otherwise sensible signal alteration relative to a background or reference condition. The alteration itself may take any of many forms, such as signal reduction, signal increase, frequency shift, appearance of a spectral feature, loss of a spectral feature, a change in relaxation or decay time, and/or the like. The alteration may comprise one or more of these and other forms simultaneously. A change in the duration of signal decay time and a change in an SCP value, as discussed above, are merely examples of many possible alterations that may be employed.

The NMR apparatus 10 may be used to detect an object 180 or several objects in a sample material 150 that is allowed to flow through the sensing region 12 of the apparatus. It may be useful to flow the sample material in this manner in any of a number of applications, such as one in which a large volume of sample material is to be is to be analyzed. By way of illustration, in a situation in which sample material flow is employed, the sample material in the sensing region may be excited to magnetic resonance and the resulting magnetic resonance signal detected. The detected signal may be associated with an appropriate SCP value. This process may be repeated another time, or may be several times, as the sample material flows through the sensing region. The data obtained may be plotted as shown in the graphical representation 230 of SCP versus time step in the middle of FIG. 1b. Each time step refers to a time at which an excitation/detection occurs. The time steps may or may not be fairly arbitrary. For example, the time steps may or may not be uniform in duration, or uniformly periodic. In a situation in which there is initially no object in the sample material in the sensing region at a time of excitation/detection, the SCP value may be relative high. A few such relatively high SCP values 240 appear in the left of the plot 230. In a situation in which the flowing sample material then brings an object into the sensing region at a time of excitation/detection, the SCP value may drop, as illustrated by the relatively lower SCP values 250 that appear in the middle of the plot 230. In a situation in which the flowing sample material causes the detected object to flow out of the sensing region and brings no new object into the sensing region at a time of excitation/detection, the SCP value may rise, as illustrated by the relatively higher SCP values 260 shown in the right of the plot 230. These later SCP values 260 may be similar to the initial SCP values 240, as both situations show the absence of a detected object.

In situations in which relatively low flow rates are used, such as those just described, the resulting output signals may not be that different or appreciably different from those resulting when a stationary sample material is used. The ability to detect objects may be compromised at higher flow rates, as higher flows alter the resulting signal. In the situations described in relation to FIG. 1b, where an object 180 is absent or present, respectively, the sinusoidal output signals 200 and 220 decay over time as the excited sample material exits the sensing region 12. If a higher flow rate were employed in each of these situations, the duration of the decay of the resulting reference output signals would decrease. In such a case, the distinction between the "normal" or reference output signal when no object is present and the output signal when an object is present would be harder to discern. By way of explanation, the relatively long-lived portion of the object-free signal 200 is relatively important in the determination of whether or not an object is present. At a higher flow rate, this otherwise long-lived portion of the object-free signal would be foreshortened, and thus harder to discern.

As mentioned previously, there are various forms of signal alteration that may be used to show the presence or absence of an object or other localized heterogeneity in the sensing region. The use of relatively high flow rates may compromise detection via such forms of signal alteration. By way of example, a distinctive spectral feature may become blurred or the size of a signal increase or a signal decrease may become relatively small, such that distinguishing object-related signal alterations from random fluctuations may become more difficult. By way of illustration, in a situation like that described above in relation to the graphical representation 230 of FIG. 1b, but wherein a relatively higher flow rate is employed, a resulting SCP versus time step plot might appear as shown in the graphical representation 270 of FIG. 1b. A comparison of the graphical representations 230 and 270 reveals more "noise" in the data for the latter, making it harder to discern whether or not an object has passed through the NMR device. That is, comparatively, the SNR, the detection capability, and/or the detection reliability associated with the higher flow rate situation will be lower than that associated with the lower flow rate situation. In a situation involving a very fast flow rate, it may be quite difficult to impossible to adequately or reliably detect the presence or absence of the object in the sensing region 12 of the apparatus 10.

In some NMR applications, when a SNR associated with the data output is undesirably low, a technique of signal averaging may be used to try to improve the SNR and thus the data output. Signal averaging may take the form of repeating excitation of the coil and detection of a signal from a sample multiple times and summing the resulting signals. If the sample is the same in each repetition, such a summation may provide a better SNR. Signal averaging may be a useful tool in a variety of applications, such as a flowing-sample material application in which the portion of the sample material in the sensing region at any given moment is more or less, or substantially, the same. While signal averaging techniques may be employed to address a low SNR in some applications, it may not be that helpful in the detection of an object 180 in a sample material 150 flowing through the sensing region 12 of an apparatus 10 because the signal is changing, and may not be very helpful at all when such a sample material is flowing at a flow rate that is so fast that that the object is in the sensing region for no more than a single time step.

An operational definition of slow versus fast flow rates for any given application may be based on the ability to detect the presence or absence of an object via NMR and/or the breakdown of that ability. A low or slow flow rate is one in which a clear indication of the presence of an object may be detected via an SCP versus time step plot, such as that described above in relation to plot 230 of FIG. 1b. A medium flow rate is one in which such an indication is less clear, but may still be of some use in determining the presence of an object. An overly high or fast flow rate is one in which such an indication is not definitive. The boundary between fast versus slow, unsuitable and suitable, and the like, may depend on a number of factors, such as the particular apparatus employed, how it is employed, how it is operated, the sample material being analyzed, the objects being analyzed, and/or the like. A fast flow rate for one device may be considered a slow flow rate for a different device.

While a reduction in the flow rate of a sample material under study may ameliorate one or more of the above-mentioned challenges, such a reduction may not be desirable for a variety of applications, such as an application in which a rapid sample material flow rate is desirable. By way of example, in an application in which the fast or immediate gathering of useful data is desirable, such as in the study of a biological sample material in a medical emergency, for example, reduction of the flow rate of the sample material sample may be undesirable or unacceptable.

Various apparatus that are useful for the probing of flowing sample materials via NMR detection in a variety of applications are now described. Such apparatus may be useful in applications involving sample materials flowing through a sensing region at anywhere from a relatively slow rate to a relatively rapid rate. By way of example, such an apparatus may allow for NMR detection in the situations described above in relation to FIG. 1, in which sample materials flow through the sensing region at a variety of flow rates, including relatively fast flow rates. The various NMR apparatus now described may comprise multiple coils instead of the single excitation/detection coil employed in the NMR apparatus described above in relation to FIG. 1. Such apparatus may facilitate detection of the longer-lived portions of magnetic resonance output signals and/or may facilitate processing of magnetic resonance output signals via signal-averaging techniques.

Figure 2A:
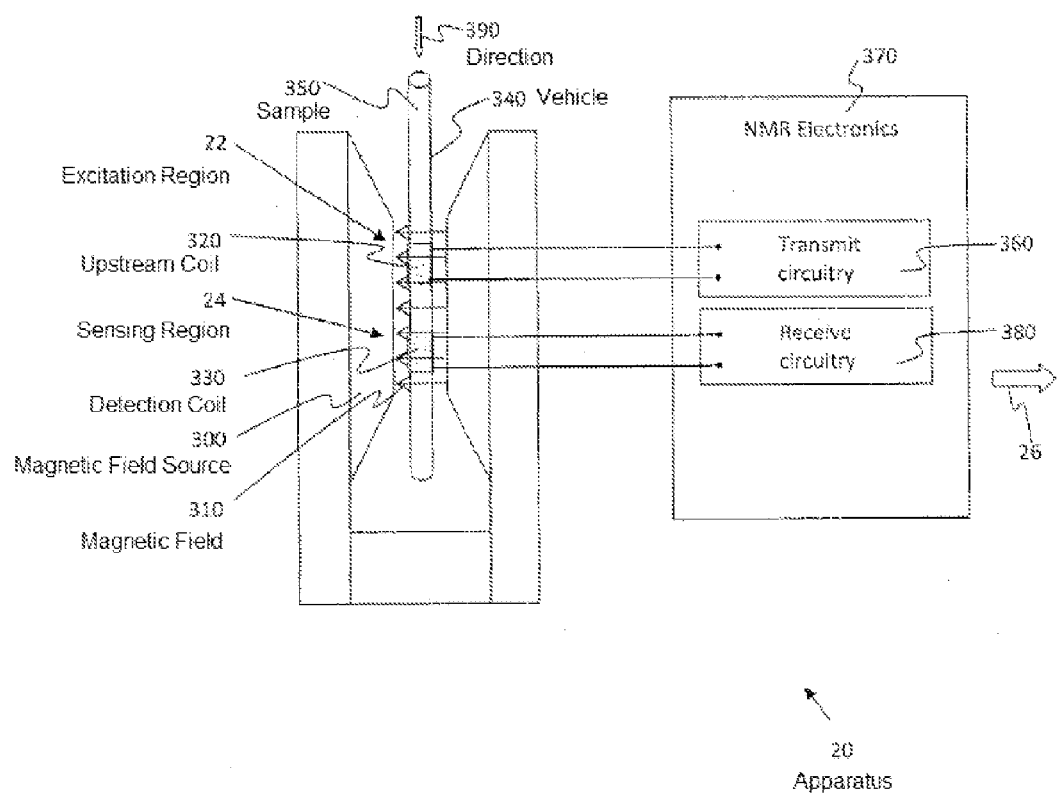
FIG. 2a is a schematic depiction of an apparatus or a device that may be used for NMR detection.

An apparatus 20 for NMR detection according to one embodiment is now described in relation to FIG. 2. As shown in FIG. 2a, the apparatus 20 comprises a vehicle 340, such as a sample material conduit, for example, for containing a sample material sample 350 as it is either held therein, when the sample material is not in flow, or flows therethrough in direction 390 through the excitation region 22 and the sensing region 24 of the apparatus.

The apparatus 20, which may be an NMR spectrometer, for example, comprises a magnetic field source 300, such as a magnet, that is sufficient to provide a substantially uniform or homogeneous magnetic field 310 in an active region which encompasses the excitation region 22 and the sensing region 24 of the apparatus. As shown, the NMR apparatus comprises at least two coils disposed in the magnetic field 310, including an upstream excitation coil 320 that that is placed near or surrounds the excitation region 22 and a downstream detection coil 330 that is placed near or surrounds the sensing region 24. The upstream coil 320 is of a construction sufficient for excitation of the sample in the excitation region 22 and the downstream coil 330 is of a construction sufficient for detection of a signal from the sample in the sensing region 24. The upstream and downstream coils may be operably coupled to NMR electronics 370, which may comprise transmit circuitry 360, and receive circuitry 380, respectively sufficient for transmission of excitation energy or power, such as rf energy, for example, to the coil 320 to excite the sample in the excitation region 22 to a state of magnetic resonance, and for reception of magnetic resonance signals, such as voltage signals, for example, from the excited sample in the sensing region 24.

Figure 2B:
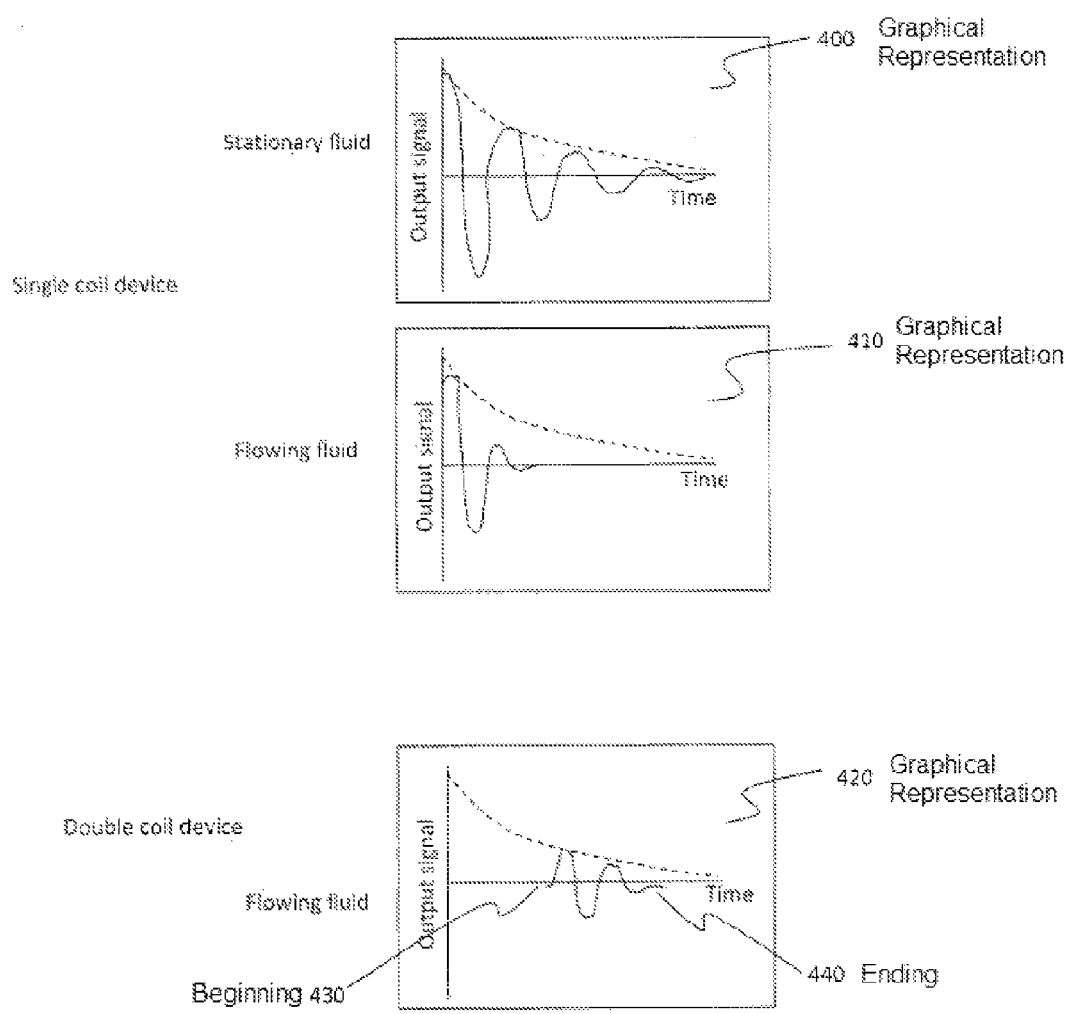
FIG. 2b shows graphical representations of output signal versus time corresponding to various NMR detection applications, as further described herein.

The NMR electronics 370 may comprise any suitable arrangement of components, such as any suitable arrangement or housing of components together or separately, for example. The NMR electronics 370 may comprise any components suitable for production, processing, manipulation (such as transforming, for example), communication, and/or the like, of the excitation energy, and any components suitable for the reception, processing (such as filtering, for example), manipulation (such as amplification, for example), communication, and/or the like of the detected signal. The NMR electronics 370 may comprise any software and/or hardware components suitable for manipulation of the output of the receive circuitry 380, such as that suitable for recording and/or displaying an output signal 26 in a useful format, such as a fairly simple graphical representation of the output signal versus time, for example, as shown in FIG. 2b. The output signal may be presented as a decaying sinusoid, as shown in the bottom-most plot 420 of FIG. 2b, wherein the time associated with the beginning 430 of the sinusoid corresponds to the moment the sample material 350 that has been excited to magnetic resonance arrives in the sensing region 24 for detection, and wherein the resulting magnetic resonance signal lasts for a shorter or longer time as may be influenced by physical properties of, or physical processes occurring in, the excited sample material, and its time of residence in the sensing region.

When the apparatus 20 is used to detect a signal from a sample material 350 flowing therethrough, the transmitter 360 sends excitation energy or power to the excitation coil 320 to excite the portion of the sample material that is in the excitation region 22 to magnetic resonance. At this time, as the portion of the sample material that is in the sensing region 24 has not been excited, no signal will be detected via the detector coil 330. Later, as sample material flow brings the portion of the sample material that was excited into the sensing region 24, a magnetic resonance signal will be detected via the detector coil 330.

By way of illustration, graphical representations 400 and 410 of output signal versus time as described in connection with apparatus 10 of FIG. 1 are shown in FIG. 2b. Graphical representation 400 corresponds to an application in which the sample material 150 is stationary or flowing very slowly through apparatus 10. In such a case, the detected signal is appreciable or substantial, perhaps maximal. Graphical representation 410 corresponds to an application in which the sample material 150 is flowing more quickly. In such a case, the detected signal is comparatively foreshortened, as the portion of the sample material that is excited leaves the sensing region more quickly.

Further by way of illustration, graphical representation 420 of output signal versus time corresponds to an application similar to that just described but employing a sample material flowing through apparatus 20 shown in FIG. 2a, Initially, there is no magnetic resonance to detect, as the excited sample material is upstream of the sensing region 24. As such, no output signal results. Later, once the excited sample material has flowed to the sensing region, magnetic resonance is detected and the beginning 430 of an output signal results. Still later, once the excited sample material has flowed out of the sensing region 24, magnetic resonance no longer exists for detection and the ending 440 of the output signal results. The properties or characteristics of the resulting output signal, such as that shown in plot 420, may depend on a variety of factors, such as the velocity of the sample material, the chemical or physical properties of the sample material, the separation between the excitation and detection coils, the sizes or lengths of these two coils, and/or the like.

In the apparatus 20 of FIG. 2a, the excitation coil 320 and the detection coil 330 may be arranged in any suitable manner. A suitable arrangement of these coils can facilitate observation of part of the long-lived portion of the NMR signal obtained from a rapidly flowing sample material. Deciding on a suitable arrangement or a suitable operating condition may be accomplished in a variety of suitable ways. By way of illustration, in a case in which the flow velocity may be set, one or more feature(s) of the apparatus, such as the lengths of the coils and/or the separation of the coils, for example, may be suitably arranged accordingly. Further by way of illustration, in a case in which the lengths of the coils and/or the separation of the coils, for example, may be set, the velocity of the sample material may be suitably chosen accordingly. In either such case, it is possible to establish a suitable operational condition for the apparatus and/or for the application to enable observation of part of the long-lived portion of the NMR signal.

By way of illustration, a suitable design of the apparatus 20 and/or a suitable arrangement of the coils thereof may be arrived at upon consideration of the portions of the sample material that give rise to the beginning and end parts of the detected signal. The beginning parts 430 of the detected signal shown in plot 420 are associated with the part of the sample material that was located near the downstream end of the excitation coil 320 when the sample material was excited. The detected signal may begin when this part of the sample material first arrives at the detector coil 330. The end parts 440 of the detected signal shown in plot 420 are associated with that part of the sample material that was near the upstream end of the excitation coil when the sample material was excited. The detected signal may end when this part of the sample material exits from the downstream end of the detection coil 330.

Merely by way of example, various apparatus parameters may be considered and selected based on the assumption that all of the sample material 350 moves with a common velocity and demonstrate one way to calculate the device design parameters. In a case in which the velocity of the sample material is fixed and known, suitable coil geometry may be derived in the manner now described. In this derivation, $t_b$ and $t_e$ respectively represent a beginning time and an ending time of the portion of the signal that is of interest; $L_e$ and $L_d$ respectively represent a length of the upstream excitation coil and the downstream detection coil; s represents a separation distance between the two coils, measured between the downstream end of the excitation coil and the upstream end of the detection coil; and v represents a velocity of the flowing sample material. At a given flow velocity, the detected signal will begin at approximately $t_b=s/v$ and end at approximately $t_e=(s+L_e+L_d)/v$. Based on these equations, the spacing of the two coils may be chosen so that $s=vt_b$, and the sum of the lengths of the coils may be chosen via the equation $(L_e+L_d)=v(t_e-t_b)$. These individual lengths of the coils need not be constrained. These lengths may be chosen to be identical ($L_e=L_d=(t_e-t_b)/2$, for example) or any other suitable lengths.

Figure 4A:
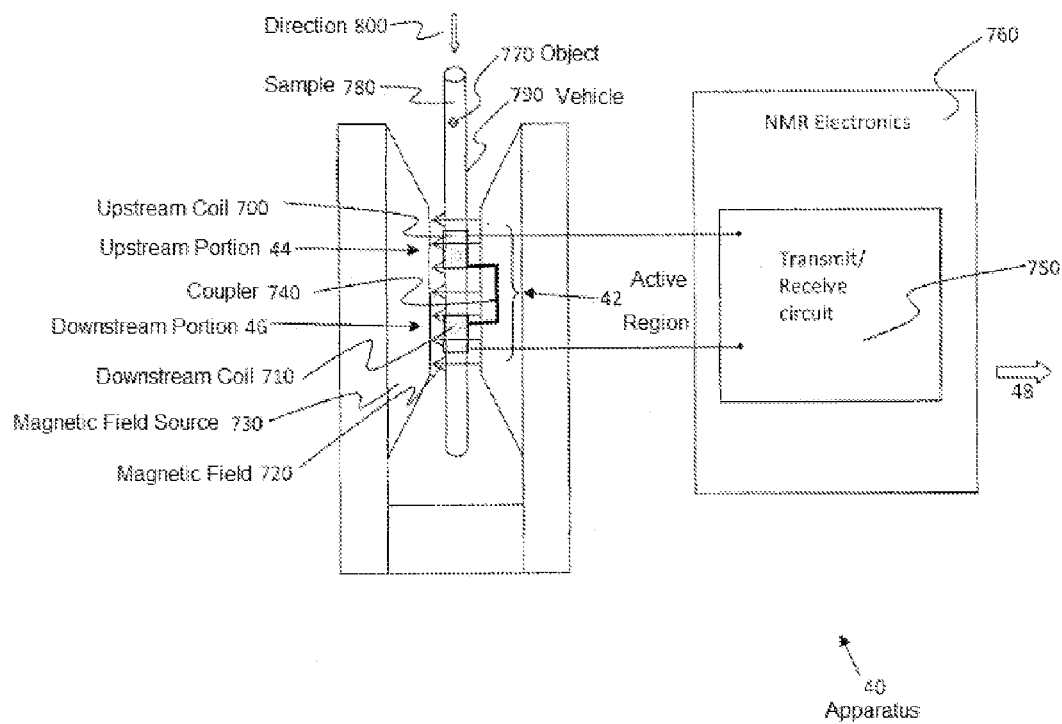
FIG. 4a is a schematic depiction of an apparatus or a device that may be used for NMR detection.
Figure 6:
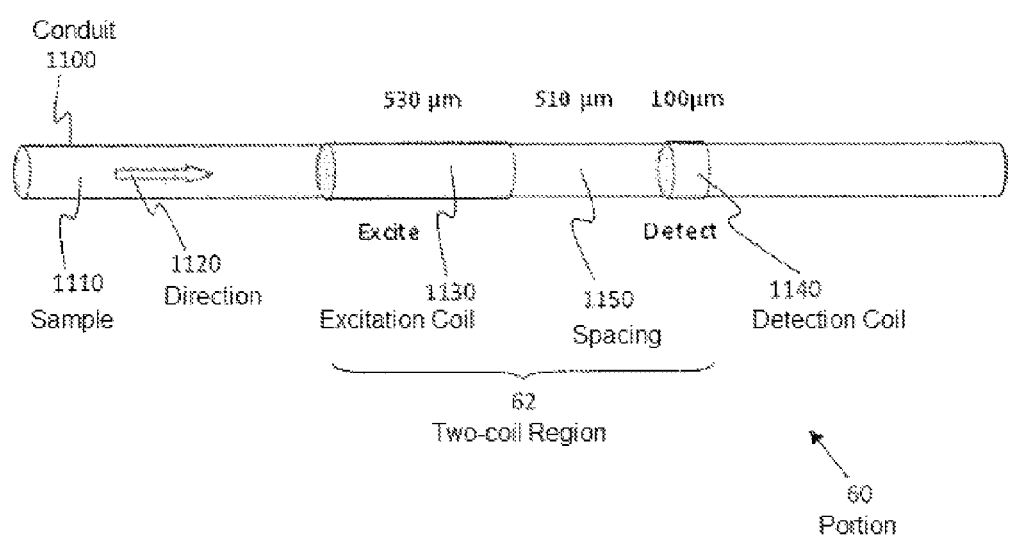
FIG. 6 is a schematic depiction of a portion of an apparatus comprising a conduit and two coils that may be used in an NMR detection application, as further described herein.

A suitable design of the apparatus 20 and/or a suitable arrangement of the coils thereof may be arrived in any other suitable manner, such as that as now described merely by way of illustration. The length of the excitation coil may be chosen to be the same length as the gap separating the two coils ($L_e=s$), such that $L_d=v(t_e-2t_b)$. This approach may be useful in a situation in which all parts of the sample volume are excited and subject to detection as it continuously flows through the apparatus, as is illustrated in FIGS. 4a and 6. In such a situation, the sample material in the excitation region may be excited at time intervals of s/v, and magnetic resonance from the sample material in the sensing region may produce an output signal continuously. Data acquisition need not be triggered by the intermittent, periodic, or pulsed excitation. However the produced output signal will still be continuous due to the continuous flow that is occurring.

Merely by way of example, in an apparatus having previously fixed coil locations and sizes, the sample flow velocity may be chosen such that a part or parts of the long-lived portion of the output signal may be observed. Using variables provided above, a beginning time and an ending time of the portion of the signal that is of interest may be determined using the $t_b=s/v$ and $t_e=(s+L_e+L_d)/v$ equations, respectively. The velocity may be chosen such that $v=s/t_b$ to provide an appropriate time for the beginning of signal detection. The ending time of signal detection may then be fixed (not independently controlled) at $t_e=t_b(s+L_e+L_d)/s$. If a different ending time $t_e$ were desired, the velocity of the sample flow could be adjusted according to the equation $v=(s+L_e+L_d)/t_e$. The sample velocity may be set at various velocity settings and data acquired at each of the velocity settings to obtain the complete output signal between the desired $t_b$ and $t_e$ values.

The illustrative approaches described above for design and use of the apparatus 20 are approximate for any of a variety of possible reasons. By way of example, a reason may be that the beginning time and the ending time of signal detection or output may not be sharply defined, as the output signal may wax and wane gradually, for example. Further by way of example, a reason may be that the velocity of the flowing sample material may vary across the cross-section of the sample material conduit, as may be appreciated upon consideration of the parabolic flow profile associated with laminar flow, for example. In a practical implementation, the approaches and/or equations described above may be used as a guide for design and/or operation of an NMR apparatus, such as the apparatus 20 of FIG. 2. It may be desirable to optimize such design and/or operation in any suitable manner, such as by making adjustments to various design and/or operational parameters based on experiment, trial and error, and/or the like. The foregoing approaches and/or equations are merely illustrative, as other suitable approaches and/or equations may be used to arrive at suitable design and/or use parameters for various NMR apparatus described herein.

An example of one of the many possible applications of the apparatus 20 of FIG. 2 is the detection of an object or objects (not shown) in a flowing sample material. The apparatus may facilitate obtaining the long-lived portion of a magnetic resonance output signal. When this long-lived portion is the portion of the signal that is relatively or most sensitive to whether or not there is an object in the sample material, the apparatus 20 of FIG. 2 facilitates detection of such an object. This may be the case even at a flow rate that would compromise such detection via an NMR apparatus such as the apparatus 10 of FIG. 1.

By way of illustration, it may be the case that the region of the magnetic resonance output signal between $t_b$ and $t_e$ is the most sensitive to the presence of an object in a sample material flowing through the apparatus 20. Based on a chosen or a desired flow rate, suitable lengths of the coils may be determined using the $L_e=s$ and $L_d=v(t_e-2t_b)$ equations discussed above and the apparatus 20 may be arranged accordingly. In such a situation, a sample material subject to detection to determine the presence or absence of an object or objects therein, may be introduced to the apparatus 20 and allowed to flow therethrough. The transmit circuitry 360 may be activated to send excitation energy or power to the upstream excitation coil 320 to excite the sample material in the excitation region 22. The excitation energy or power may be delivered in a pulsed manner, such as via pulses delivered every s/v seconds, or more or less often, such that all of the sample material is eventually excited. As excited sample material arrives in the sensing region, detection and signal acquisition takes place continuously (or quasi-continuously, if breaks in the data stream occur, such as any breaks attributable to limitations in the electronics or software, for example). The acquired signal may be processed to provide appropriate SCP values, for example, as described previously. The data may be used in any appropriate manner, such as to produce a plot of SCP versus time, for example, to determine if an object or objects have passed through the sensing region of the apparatus. Data acquired using an apparatus 20 of FIG.

2 that has been designed and/or optimized to detect that portion of the signal that is relatively important to object detection will generally have a higher SNR than data acquired from an apparatus 10 of FIG. 1.

Aspects and features of apparatus 20 of FIG. 2 and the use thereof may vary in any suitable way. Merely by way of example, more than one detector coil may be used. In such a case, a detector coil may be placed in an appropriate manner so that it facilitates acquisition of a part of the output signal, another detector coil may be so placed so that it facilitates acquisition of another part of the output signal, and so on if further detector coils are employed. Further by way of example, an upstream coil may be used to excite the sample material in the excitation region to magnetic resonance and to detect the initial portion of the resulting magnetic resonance, and a downstream coil may be used simply for detection. In this example, each of the two detected signals may be used separately or together to enhance detection accuracy and/or precision. Still further by way of example, an excitation and a detection coil may be placed adjacent to one another, with little or no gap therebetween. In another example, adjacent segments of the same coil may be used for excitation and detection, respectively. In such a case, segmentation may be accomplished in any suitable manner, such as via installation of a tap along the length of the coil, for example.

The coils used for excitation and/or detection may be any electrical structure capable of exciting and/or detecting NMR signals from the sample material. The coils may be solenoids, spiral surface coils, meanderline coils, striplines, and/or any other suitable structure. The same or different structures may be used for excitation and detection coils. The same or different structures may be used for excitation coils. The same or different structures may be used for detection coils. The various coil structures employed may be oriented with respect to one another in any appropriate manner. One or more of these possible variations may facilitate a reduction in electromagnetic coupling between structures, or an electromagnetic decoupling of structures, as may be desirable.

A suitable alteration of the magnetic field region 310 associated with the apparatus 20 may also be possible. By way of example, the apparatus 20 may be designed or arranged to provide a magnetic field of sufficient homogeneity to allow the desired NMR measurement and another magnetic field region of slightly or relatively reduced homogeneity. The upstream excitation coil may be located in the region of reduced magnetic field homogeneity and the downstream detection coil may be located in the more homogeneous magnetic field region. In such a case, the latter coil may be located such that it occupies the entire region of very high magnetic field homogeneity.

Figure 3A:
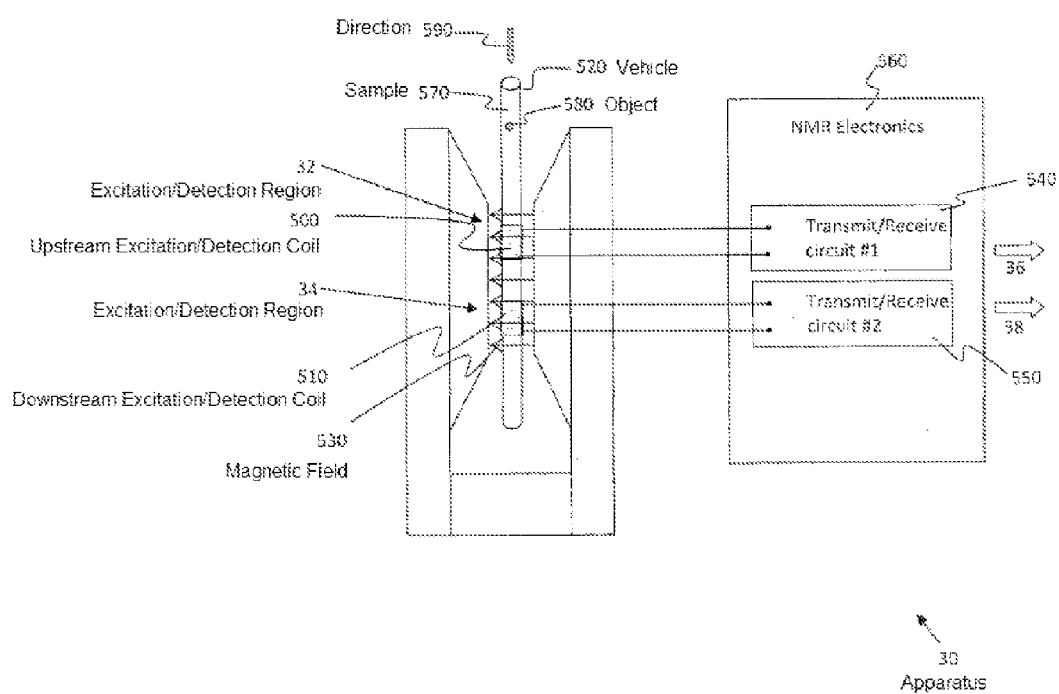
FIG. 3a is a schematic depiction of an apparatus or a device that may be used for NMR detection.

An apparatus 30 for NMR detection according to one embodiment is now described in relation to FIG. 3. (Elements of the apparatus that are unmarked in FIG. 3 may be readily understood from the description above, particularly portions thereof that pertain to the apparatus 10 of FIG. 1 and the apparatus 20 of FIG. 2.) As shown in FIG. 3a, the apparatus 30 comprises a vehicle 520, such as a sample material conduit, for example, for containing a sample material sample 570 as it is either held therein, when the sample material is not in flow, or flows therethrough in an upstream-to-downstream direction 590 through an excitation/detection region 32 and an excitation/detection region 34 of the apparatus.

The apparatus 30, which may comprise at least one NMR spectrometer, for example, comprises a magnetic field source, such as a magnet, that is sufficient to provide a substantially uniform or homogeneous magnetic field 530. As shown, the NMR apparatus comprises at least two coils disposed in the magnetic field 530, including an upstream excitation/detection coil 500 that is placed near or surrounding an excitation/detection region 32, and a downstream excitation/detection coil 510 that is placed near or surrounding an excitation/detection region 34. The upstream coil 500 is of a construction sufficient for excitation of the sample in region 32 and sufficient for detection of a signal from the sample in that region. The downstream coil 510 is of a construction sufficient for excitation of the sample in region 34 and sufficient for detection of a signal from the sample in that region.

The coil 500 may be operably coupled to NMR electronics 560, which may comprise transmit/receive circuitry 540 sufficient for transmission of excitation energy or power, such as rf energy, for example, to the coil 500 to excite the sample in the region 32 to a state of magnetic resonance, and for reception of magnetic resonance signals, such as voltage signals, for example, from the excited sample in that region. The coil 510 may be operably coupled to NMR electronics 560, which may comprise transmit/receive circuitry 550 sufficient for transmission of excitation energy or power, such as rf energy, for example, to the coil 510 to excite the sample in the region 34 to a state of magnetic resonance, and for reception of magnetic resonance signals, such as voltage signals, for example, from the excited sample in that region. The transmit/receive circuitry 540 and the transmit/receive circuitry 550 may be independent of one another.

While the NMR electronics 560 are schematically shown as a unitary element in FIG. 3a, these electronics may comprise more than one element, such as electronics sufficient for operation as two NMR spectrometers, respectively associated with the two coils, merely by way of example. It will be understood that any suitable variation of the various possible variations concerning NMR electronics, such as those described in relation to the apparatus 10 of FIG. 1 and the apparatus 20 of FIG. 2, for example, may be used in connection with the apparatus 30 of FIG. 1

In the apparatus 30 of FIG. 3a, each of the coils 500 and 510 may operate as a dual purpose excite/detect coil, as described above. As such, the apparatus may be used to obtain two separate data streams, one data stream 36 associated with coil 500 and another data stream 38 associated with coil 510. These data streams may be analyzed, processed, manipulated, and/or correlated to produce an overall data output. The overall data output may have a better or higher SNR than either of the component data streams.

An example of one of the many possible applications of the apparatus 30 of FIG. 3 is the detection of an object 580 or objects in a flowing sample material 570. The apparatus may be useful in such an application to facilitate obtaining an overall data output that has an acceptable SNR.

Figure 3B:
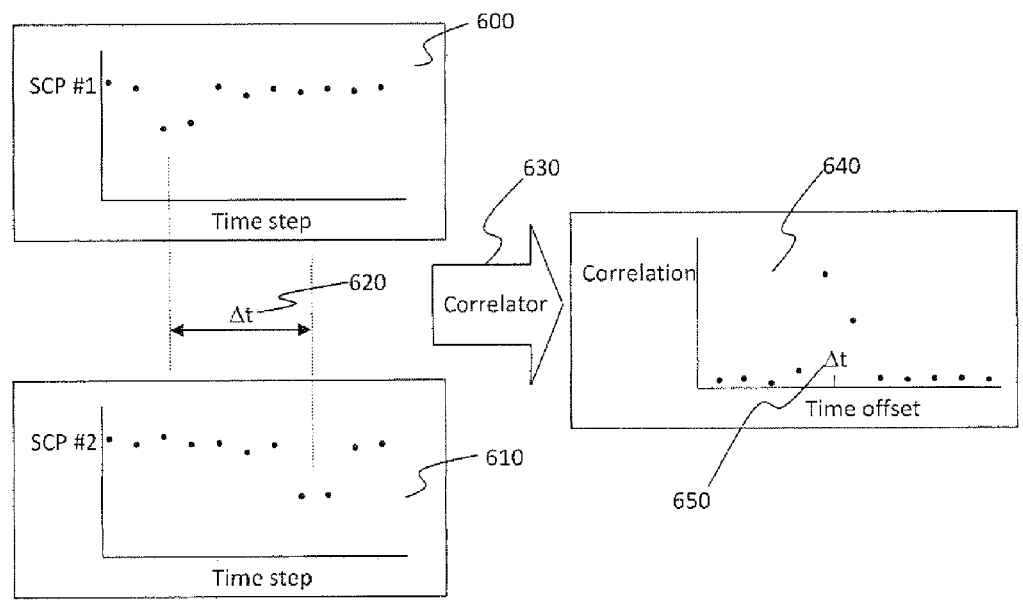
FIG. 3b shows a schematic depiction of a correlator and graphical representations of a signal characterization parameter versus time step and correlation versus time offset corresponding to various NMR detection applications, as further described herein.

By way of illustration, if it is assumed that an output signal 36 or 38 obtained using excitation/detection coil 500 or 510 at any time step is sensitive to the presence or the absence of an object 580 in the sample material in the associated excitation/detection region 32 or 34, then it is possible to assign the output signal a single SCP value that indicates the presence or the absence of the object. As such, a data stream 600 corresponding to data detected via coil 500 and another data stream 610 corresponding to data obtained via coil 510, as shown in FIG. 3b, can be obtained in a manner such as that previously described in relation to FIG. 1. The data stream 600 and the data stream 610 may be independent data streams in the form of SCP versus time step plots, as shown. As shown in FIG. 3b, the two data plots may be similar, in that they may show a high total signal value in the "normal" or reference condition in which no object is present for detection and decreased total signal value in which the object is present and detected. As also shown in FIG. 3b, the two data plots may have a common time axis. In this application, any object in the sample material passes through detection region 32 and detection region 34 in succession. As such, a time delay Δt 620 between the decrease in the total signal level shown in plot 600 and the decrease in the total signal level shown in plot 610 may be observed. Any such time delay 620 corresponds to the time it takes for such an object to travel the distance between the two coils.

As two separate data streams are generated in this example, signal averaging can be used to obtain an overall data output. Signal averaging may facilitate obtaining an overall data output with a good SNR. Simple signal averaging involving summing up the two data streams may not be helpful in view of the time delay 620 discussed above. However, when the time delay 620 has a known value, signal averaging involving time-shifting the data streams according to the time delay and summing up the time-shifted data streams may be helpful.

Whether the time delay is known or unknown, yet another signal averaging approach may be used. By way of example, it is possible to use a correlator 630, comprising suitable hardware and/or software, to correlate the two data streams. The correlator 630 may comprise any suitable hardware and/or software sufficient to obtain an applicable correlation function, such as the correlation function (a plot of correlation versus time offset) 640 shown in FIG. 3b, for the two data streams. As shown, the correlation function or plot may show a peak at a time offset Δt 650 that is equal to the time delay Δt 620 corresponding to the time it takes for the object to move from the upstream coil to the downstream coil. This peak may serve as a signature of passage of the object through the coils of the apparatus 30. As the correlation function is formed from two independent data streams, each of which is affected by passage of the object, the visibility of the object-related peak in the correlation function may be greater than any object-related peak or valley appearing in either of the individual data streams. As shown in FIG. 3b, the SNR of the correlation function is relatively high, as the peak of the correlation is relatively high and quite visible relative to the random fluctuations in the non-peak regions of the correlation function. As such, the SNR of the correlation function is relatively high in comparison to the SNR associated with either of the individual data streams.

The correlation approach may be of benefit in the application just described. The SNR benefit of such an approach in NMR applications involving flowing samples may be the same in theory as the benefit associated with simple signal averaging in such applications involving stationary samples. It is contemplated that further SNR benefit may be accomplished when more than two excitation/detection coils in an apparatus such as apparatus 30 of FIG. 3. In such a case, the SNR benefit may be proportional to the square root of the number of independent data streams employed.

Any suitable variation of the various possible variations described in relation to the apparatus 10 of FIG. 1 and the apparatus 20 of FIG. 2, the operation thereof, and/or the use thereof, may be used in connection with the apparatus 30 of FIG. 3. As each of the excitation/detection coils of the apparatus 30 is separately employed for both excitation of sample material and detection of signal from excited sample material in separate regions, some details of the design or construction of the excitation/detection coils used in the apparatus 30, such as the sense of winding of the coils, for example, may not have much impact the data sets obtained via these coils.

Figure 3C:
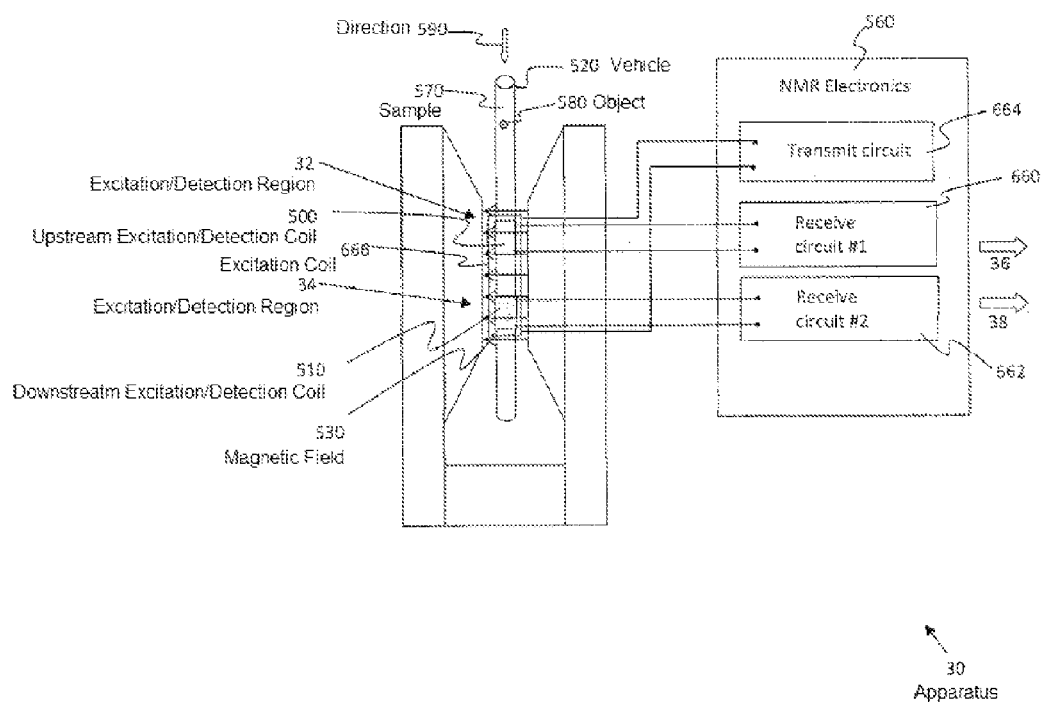
FIG. 3c is schematic depiction of another apparatus or device that may be used for NMR detection.

The apparatus 30 of FIG. 3 may be altered in any suitable manner. Merely by way of example, another version of apparatus 30 is shown in FIG. 3c. Such an apparatus may comprise an excitation coil 666 sufficient to excite the sample to magnetic resonance in all detection regions of the apparatus. Such an excitation coil may be larger than that described above, and may be located in a vicinity of the coils 500 and 510 and regions 32 and 34 associated with the coils; merely by way of example. In such an apparatus, the coils 500 and 510 may be used solely to detect magnetic resonance signals. The excitation coil 666 may be operably coupled to suitable transmit circuitry of the NMR electronics, while the coil 500 and 510 may be operably coupled to receive circuitry 660 and 662 of the NMR electronics 560, such as two independent receive circuitries, for example. When the receive circuitries are independent, signals 36 and 38 from the two receive circuitries 660 and 662, respectively, may be processed in any suitable manner, such as any of those described above.

The apparatus 30 of FIG. 3 may be employed in any suitable manner, such as one that differs from that described above. Merely by way of example, two or more signals 36 and 38 from the transmit/receive circuitry 540 and the transmit/receive circuitry 550, or from the receive circuitry 660 and the receive circuitry 662, may be combined. Such a combining may comprise adding or subtracting the signals to produce a single data stream, which may be processed to produce useful information, such as an SCP versus time plot, for example. As a single data stream is produced, it is possible to produce useful information without correlation.

When the signals are combined, such as in the manner just described, the single data stream may be made using linear or non-linear mathematical and/or electrical transformation. Such a transformation may be such that an overall cancellation occurs such that there is no overall signal when there is no object in any detection region. In such a situation, an SCP value may be chosen to be indistinguishable from zero, for example. When an object of interest appears in any detection region, it may disrupt the overall cancellation that would otherwise occur, such that a non-zero SCP value results. In this manner, passage of an object through any detection region may be detected or confirmed.

This variation in the use of the apparatus 30 may be advantageous in that it may facilitate flexibility in the manner in which data of interest may be manipulated. By way of example, it may be possible to obtain sufficiently accurate cancellation even when the detection coils are mismatched. Further by way of example, it may be possible to reduce computational complexity in the analysis of the data. Still further, it may be advantageous to employ the variation in the use of the apparatus 30 described above such that a nulled detector produces a signal only when an object of interest is present in or passes through a detection region.

An apparatus 40 for NMR detection according to one embodiment is now described in relation to FIG. 4. (Elements of the apparatus that are unmarked in FIG. 4 may be readily understood from the description above, particularly portions thereof that pertain to the apparatus 10 of FIG. 1, the apparatus 20 of FIG. 2, and the apparatus 30 of FIG. 3.) As shown in FIG. 4a, the apparatus 40 comprises a vehicle 790, such as a sample material conduit, for example, for containing a sample material sample 780 as it is either held therein, when the sample material is not in flow, or flows therethrough in an upstream-to-downstream direction 800 through a generally active region 42 of the apparatus.

The apparatus 40, which may comprise at least one NMR spectrometer, for example, comprises a magnetic field source 730, such as a magnet, that is sufficient to provide a substantially uniform or homogeneous magnetic field 720. As shown, the NMR apparatus comprises at least two coils disposed in the magnetic field 720, including an upstream coil 700 that is placed near or surrounding an upstream portion 44 of the region 42, and a downstream coil 710 that is placed near or surrounding a downstream portion 46 of the region 42. The upstream coil and the downstream coil are operably or electrically coupled in series, via a coupler 740. The coils are of a construction sufficient for excitation of the sample in the upstream portion 44 and the downstream portion 46 of region 42 and for detection of a signal from the sample in those regional portions.

The coils may be operably coupled to NMR electronics 760, which may comprise transmit/receive circuitry 750 sufficient for transmission of excitation energy or power, such as rf energy, for example, to the coils to excite the sample in the regional portions 44 and 46 to a state of magnetic resonance, and for reception of magnetic resonance signals, such as voltage signals, for example, from the excited sample in those regional portions. The NMR electronics 760 may comprise electronics sufficient for operation of a single-channel NMR spectrometer, merely by way of example. It will be understood that any suitable variation of the various possible variations concerning NMR electronics, such as those described in relation to the apparatus 10 of FIG. 1, the apparatus 20 of FIG. 2, and the apparatus 30 of FIG. 3, for example, may be used in connection with the apparatus 40 of FIG. 4.

In the apparatus 40 of FIG. 4a, the coils in series may be operated more or less in concert to produce a single one data stream 48 associated with excited sample material flowing through the upstream portion 42 and the downstream portion 44 of the generally active region 42. As there is a single channel for receiving a detected signal, which amounts to a summation of a component signal associated with the upstream coil 700 and a component signal associated with the downstream coil 710, the apparatus produces a single data stream 48. The data stream may be analyzed, processed, manipulated, and/or correlated to produce any useful overall data output. The overall data output may have a better or higher SNR than would an individual data stream associated with operation of an individual coil alone.

An example of one of the many possible applications of the apparatus 40 of FIG. 4 is the detection of an object 770 or objects in a flowing sample material 780. The apparatus may be useful in such an application to facilitate obtaining an overall data output that has an acceptable SNR.

Figure 4B:
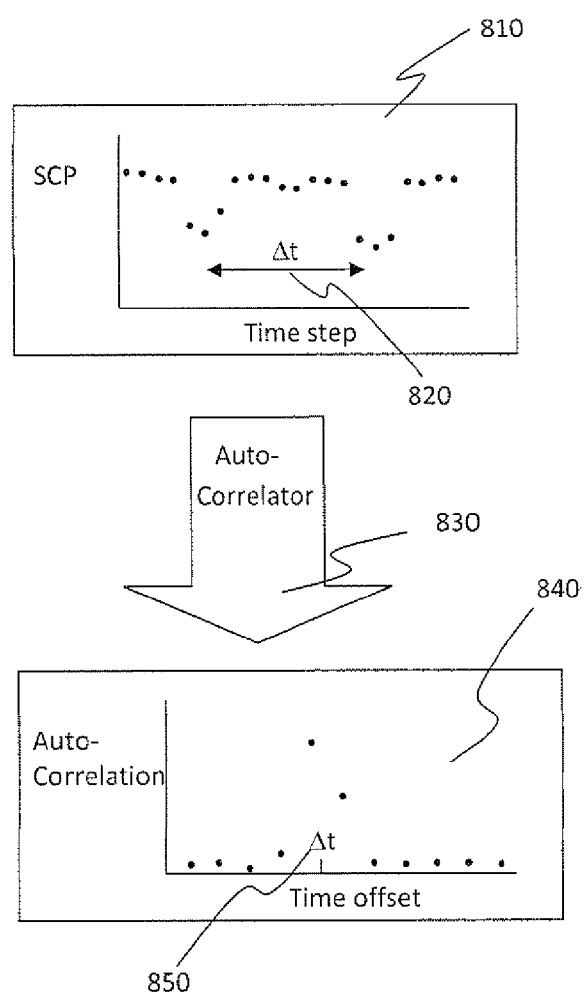
FIG. 4b shows a schematic depiction of an auto-correlator and graphical representations of a signal characterization parameter versus time step and auto-correlation versus time offset corresponding to various NMR detection applications, as further described herein.

By way of illustration, if it is assumed that an object 770 has an effect on a signal as described previously, then the result of an object passing through the apparatus 40 would be an output signal 48 that could be processed to provide an SCP versus time step plot 810 showing two dips separated by a time gap Δt 820, as shown in FIG. 4b. This time gap or transit time corresponds to the period in which the object 770 is between the two coils and thus is not detected.

As the data set comprises two independent regions of data (such as the two dips shown in plot 810, for example) that indicate of the passage of the object, it is amenable to a form of signal averaging. Signal averaging may facilitate obtaining an overall data output with a good SNR.

By way of example, it is possible to use an auto-correlator 830, comprising suitable hardware and/or software, to correlate the two data regions of interest. The auto-correlator 830 may comprise any suitable hardware and/or software sufficient to obtain an applicable auto-correlation function, such as the auto-correlation function (a plot of auto-correlation versus time offset) 840 shown in FIG. 4b, for the two data regions of interest. As shown, the auto-correlation function or plot may show a peak at a time offset Δt 850 that is equal to the time gap Δt 820 corresponding to the time it takes for the object to move from the upstream coil to the downstream coil. This peak may serve as a signature of passage of the object through the coils of the apparatus 40. As the correlation function is formed from two independent regions of data, each of which is affected by passage of the object, the visibility of the object-related peak in the correlation function may be greater than any object-related peak or valley corresponding to either of the individual regions of data. As shown in FIG. 4b, the SNR of the correlation function is relatively high, as the peak of the correlation is relatively high and quite visible relative to the random fluctuations in the non-peak regions of the correlation function. As such, the SNR of the correlation function is relatively high in comparison to the SNR associated with either of the individual regions of data of interest. The auto-correlation approach may thus be of benefit in the application just described.

Any suitable variation of the various possible variations described in relation to the apparatus 10 of FIG. 1, the apparatus 20 of FIG. 2, the apparatus 30 of FIG. 3, the operation thereof, and/or the use thereof, may be used in connection with the apparatus 40 of FIG. 4. The apparatus 40 of FIG. 4 may be varied in any of a variety of suitable ways, such as a variation in which the coils are operably connected in parallel, in a partially parallel configuration, in a partially series configuration, and/or in any suitable combination thereof, rather than in series. Further by way of example, the apparatus 40 may comprise more than two coils which may be configured in any suitable way, such as any of the configurations just described.

Figure 5A:
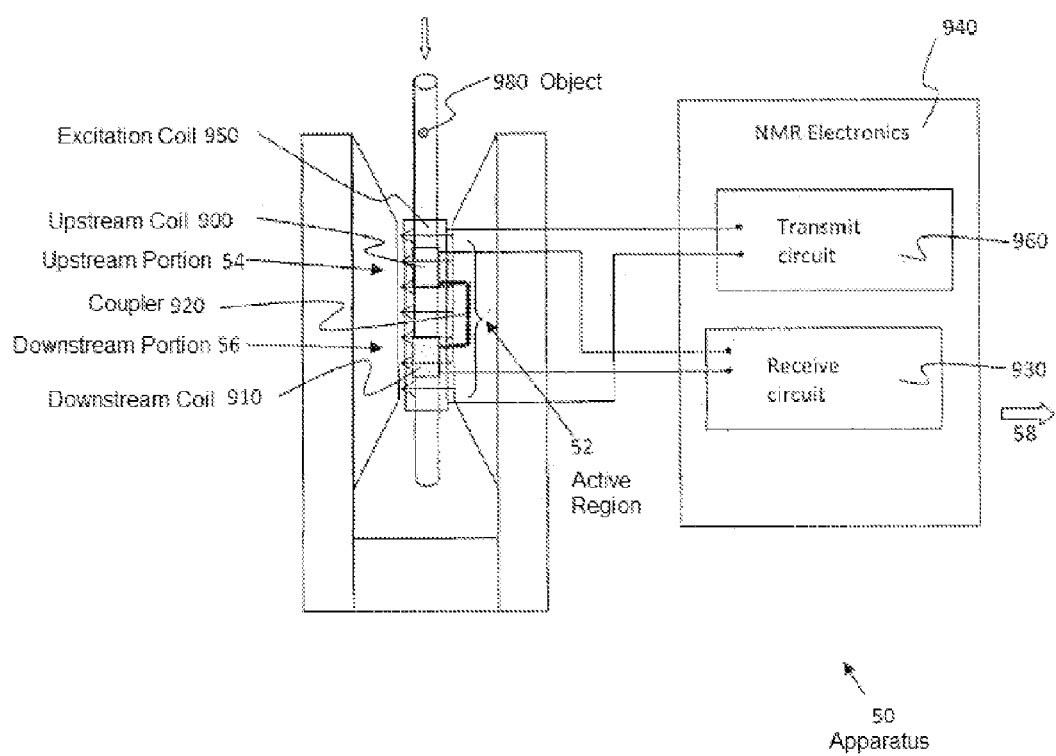
FIG. 5a is a schematic depiction of an apparatus or a device that may be used for NMR detection.
Figure 5B:
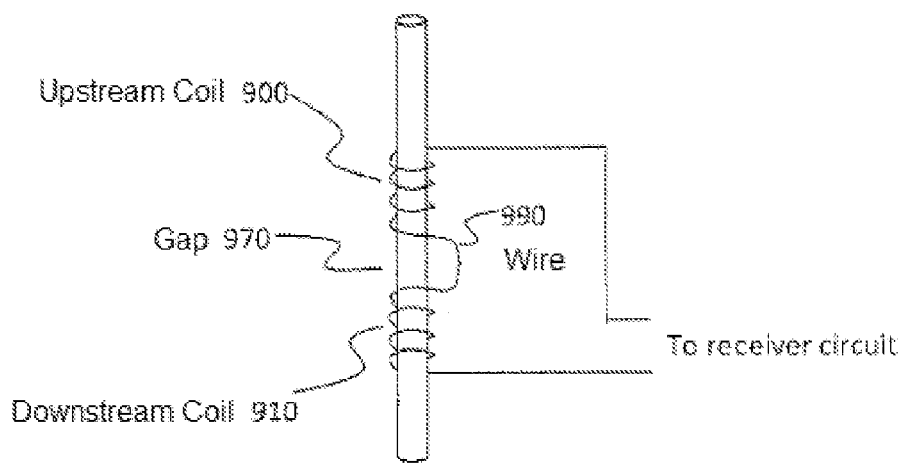
FIG. 5b is a schematic depiction of anti-sense winding associated with detection coils of such an apparatus.

An apparatus 50 for NMR detection according to one embodiment is now described in relation to FIG. 5. (Elements of the apparatus that are unmarked in FIG. 5 may be readily understood from the description above, particularly portions thereof that pertain to the apparatus 10 of FIG. 1, the apparatus 20 of FIG. 2, the apparatus 30 of FIG. 3, and the apparatus 40 of FIG. 4.) As shown in FIG. 5a, the apparatus 50 comprises a vehicle, such as a sample material conduit, for example, for containing a sample material sample as it is either held therein, when the sample material is not in flow, or flows therethrough in an upstream-to-downstream direction through a generally active region 52 of the apparatus.

The apparatus 50, which may comprise at least one NMR spectrometer, for example, comprises a magnetic field source, such as a magnet, that is sufficient to provide a substantially uniform or homogeneous magnetic field 910. As shown, the NMR apparatus comprises at least two coils disposed in the magnetic field 910, including an upstream detection coil 900 that is placed near or surrounding an upstream portion 54 of the region 52, and a downstream detection coil 910 that is placed near or surrounding a downstream portion 56 of the region 52. The upstream coil and the downstream coil are operably or electrically coupled in series, via a coupler 920. The detection coils are of a construction sufficient for detection of a signal from the sample in those regional portions. The apparatus 50 comprises an excitation coil 950 which is larger, such as in diameter and in length, for example, than the detection coils 900 and 910. The coil 950 is placed near or surrounding the generally active region 52. The excitation coil 950 may encompass the coils 900 and 910 as shown in FIG. 5a. The excitation coil 950 is of a construction sufficient for excitation of the sample in the generally active region 52 of the apparatus. The excitation may be substantially uniform in the generally active region 52, or at least in the upstream and downstream portions 54 and 56 of that region.

The excitation coil 950 may be operably coupled to NMR electronics 940, which may comprise transmit circuitry 960 sufficient for transmission of excitation energy or power, such as rf energy, for example, to the excitation coil to excite the sample in the generally active region 52, or at least in the regional portions 54 and 56 thereof, to a state of magnetic resonance. The detection coils 900 and 910 may be operably coupled to NMR electronics 940, which may comprise receive circuitry 930 sufficient for reception of magnetic resonance signals, such as voltage signals, for example, from the excited sample in those regional portions.

The NMR electronics 940 may comprise electronics sufficient for operation of a single-channel NMR spectrometer, merely by way of example. The NMR electronics may produce an output signal 58 as schematically shown in FIG. 5a. It will be understood that any suitable variation of the various possible variations concerning NMR electronics, such as those described in relation to the apparatus 10 of FIG. 1, the apparatus 20 of FIG. 2, the apparatus 30 of FIG. 3, and the apparatus 40 of FIG. 4, for example, may be used in connection with the apparatus 50 of FIG. 5.

The detector coils 900 and 910 may be of anti-sense design or construction. Merely by way of example, these coils may be comprised of a single wire 990 that is wound in an anti-sense manner, with one coil 900 produced from a winding in one direction, the other coil 910 produced from a winding in the opposite direction, and a gap 970 produced in between the two coils, as shown by the anti-sense winding shown in FIG. 5b. The direction of the winding of a particular coil is arbitrary, and may be opposite of that shown in FIG. 5b. In such an arrangement, when a steady signal, such as a current signal, for example, is applied to the wire wire 990, the direction of the magnetic field produced in one of the coils is opposite the direction of the magnetic field produced in the other of the coils. As the excitation coil 950 is of a design or construction such that it excites sample material in the two detection coils 900 and 910 in the same way, signals generated in the detection coils, of anti-sense design or construction, are of opposite sign. In a situation in which the two detection coils are substantially geometrically matched and the excitation is substantially uniform, signals generated in the detection coils are substantially equal and opposite. In this situation, signal cancellation occurs such that no total signal is detected. In other words, the geometrical mismatch between the excitation coil and the matched detector coils nullifies detection.

An example of one of the many possible applications of the apparatus 50 of FIG. 4 is the detection of an object 980 or objects in a flowing sample material. The apparatus may be useful in such an application to facilitate obtaining an overall data output that has an acceptable SNR.

Figure 5C:
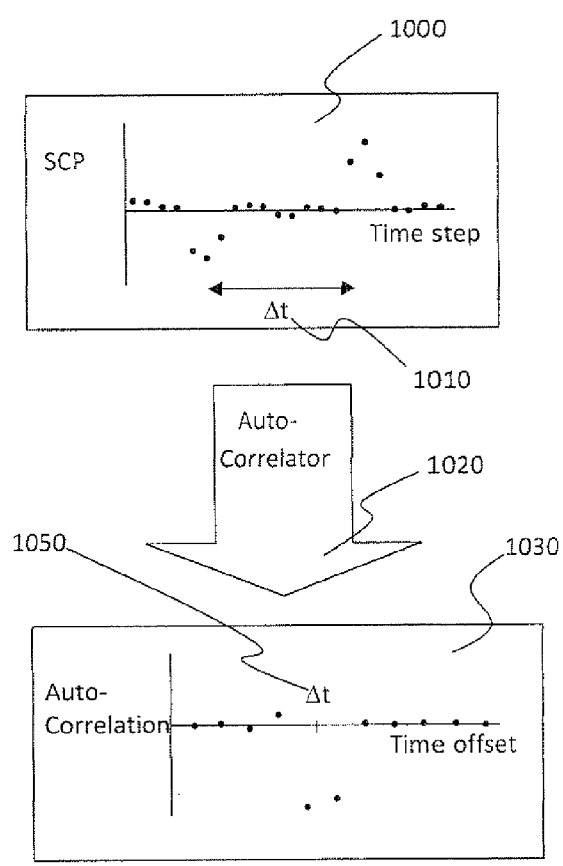
FIG. 5c shows a schematic depiction of an auto-correlator and graphical representations of a signal characterization parameter versus time step and auto-correlation versus time offset corresponding to various NMR detection applications, as further described herein.

By way of illustration, passage of an object 980 through the generally active region 52 of the apparatus disrupts the signal cancellation described above, such that detection of a signal occurs. The disruption occurs sequentially, first in the upstream coil and then in the downstream coil. The overall signal is bipolar in nature, with the initial signal showing disruption in one direction and the following signal showing disruption in the other direction. These results may be presented in a graphical representation 1000 of SCP versus time step, in a manner such as previously described, as shown in FIG. 5c. In this illustration, the plot 1000 shows a negative signal (a dip or valley), followed by a positive signal (a rise or a peak), and a time gap Δt 1010 therebetween. The time gap corresponds to the time taken for the object to travel from the upstream coil 900 to the downstream coil 910. As the plot produced is fairly distinctive, it may be useful for distinguishing an actual passage of an object from a false detection attributable to noise, for example.

The apparatus 50 may be comprise more than two detector coils. In such a case, the sense of the coil windings, the geometry of the coils, the geometry of the sample material conduit, the uniformity of the excitation, and/or the like, may be selected so that the no overall signal results when there is no object to detect in any of the regions associated with any of the coils. Such an apparatus may produce a complex signal pattern as an object passes through the detection coils. Such a complex pattern might be useful in the positive detection of the actual passage of an object through various detection regions of the apparatus.

As the data set comprises two or more independent regions of data (such as the dip and rise shown in plot 1000, for example) that indicate of the passage of the object, it is amenable to a form of signal averaging. Signal averaging may facilitate obtaining an overall data output with a good SNR.

By way of example, it is possible to use an auto-correlator 1020, comprising suitable hardware and/or software, to correlate the data regions of interest. The auto-correlator 1020 may comprise any suitable hardware and/or software sufficient to obtain an applicable auto-correlation function, such as the auto-correlation function (a plot of auto-correlation versus time offset) 1030 shown in FIG. 5c, for two data regions of interest (the valley and the peak) shown in the plot 1000. The auto-correlation function or plot may show a dip or valley at a time offset Δt 1050 that is equal to the time gap Δt 1010 corresponding to the time it takes for the object to move from the upstream coil to the downstream coil. This valley may serve as a signature of passage of the object through the coils of the apparatus 50. As the correlation function is formed from two independent regions of data, each of which is affected by passage of the object, the visibility of the object-related valley in the auto-correlation function may be greater than any object-related valley or peak corresponding to either of the individual regions of data. As shown in FIG. 5c, the SNR of the auto-correlation function is relatively high, as the valley of the auto-correlation is relatively high and quite visible relative to the random fluctuations in the non-valley regions of the correlation function. As such, the SNR of the correlation function is relatively high in comparison to the SNR associated with either of the individual regions of data of interest. The auto-correlation approach may thus be of benefit in the application just described.

Any suitable variation of the various possible variations described in relation to the apparatus 10 of FIG. 1, the apparatus 20 of FIG. 2, the apparatus 30 of FIG. 3, the apparatus 40 of FIG. 4, the operation thereof, and/or the use thereof, may be used in connection with the apparatus 50 of FIG. 5. The apparatus 50 of FIG. 5 may be varied in any of a variety, of suitable ways; such as a variation in which the coils are operably connected in parallel, in a partially parallel configuration, in a partially series configuration, and/or in any suitable combination thereof, rather than in series. Further by way of example, the apparatus 50 may comprise more than two coils which may be configured in any suitable way, such as any of the configurations just described.

EXAMPLE

An experiment was performed using a laboratory realization of an apparatus much like the apparatus 20 described above in relation to FIG. 2. Various aspects and features of the apparatus used are now described. A portion 60 of the apparatus comprised of a sample material conduit 1100, an upstream excitation coil 1130, and a downstream detection coil 1140, is shown in FIG. 6. The sample material conduit 1100 comprised a glass capillary tube having an inner diameter of about 100 μm. The sample material conduit 1100 contained a sample material 1110 which flowed in an upstream-to-downstream direction 1120, which appears as a left-to-right direction in FIG. 6. The upstream excitation coil 1130 was about 530 μm long, the downstream detection coil 1140 was about 100 μm long, and a spacing or separation distance 1150 between the two coils (as measured from the downstream end of the excitation coil to the upstream end of the detection coil) was about 510 μm long. The sample material 1110 comprised water and a gadolinium chelate, the latter added to produce a longitudinal relaxation time of about 400 milliseconds. The entire two-coil region 62 was disposed within a substantially homogenous magnetic field region associated with an appropriate field source, an NMR magnet, as may be appreciated from the arrangement of apparatus 20 shown in FIG. 2.

The apparatus was operated using a stationary sample material 1110 and using the excitation coil 1130 as a single, dual-use excitation/detection coil, as may be appreciated from various portions of the description above. The apparatus was operated in this manner to determine a suitable excitation power for maximally exciting the sample material to magnetic resonance. The apparatus was operated using a stationary sample material 1110 and using the detection coil 1140 as a dual-use excitation/detection coil, as may be appreciated from various portions of the description above. The apparatus was operated in this manner to determine the maximum magnetic resonance signal that could be detected by the detection coil.

The apparatus was then operated using a sample material 1110 in flow (via a syringe pump, not shown), the excitation coil 1130 as an excitation coil, and the detection coil 1140 as a detection coil, as may be appreciated from various portions of the description above, such as that concerning apparatus 20 of FIG. 2, for example. The apparatus was operated in this manner a number of times, using a different flow rate and acquiring the associated output data each time.

Figure 7:
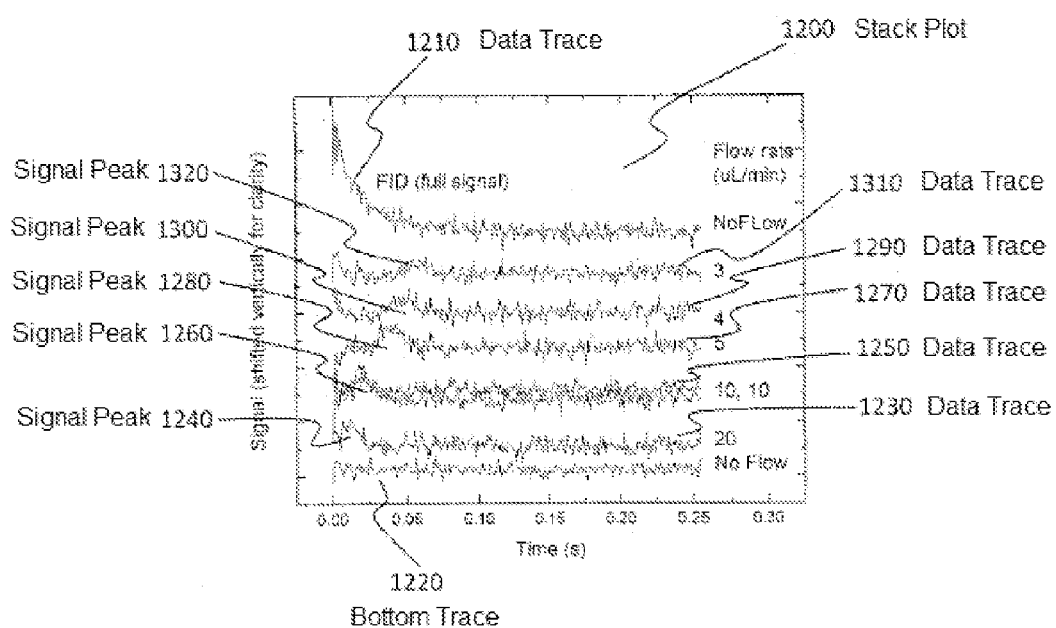
FIG. 7 is a graphical representation of detected signal versus time for an NMR detection application, as further described herein.

The resulting data are collectively shown in a stack plot 1200 of output signal (shifted vertically for clarity) versus time in FIG. 7. Each of the data traces in the stack plot 1200 comprises the amplitude envelope of the sinusoidal signal that was detected via the detection coil 1140 when the apparatus was operated using the sample material flow rate that is identified on the right side of the data trace. The top-most data trace 1210 corresponds to the signal that was detected via the detection coil 1140 when the sample material was stationary and the detection coil was used as an excitation/detection coil, as described above. This data trace 1210 represents the maximum signal that could be detected via the detection coil 1140 at any time of operation (here, from zero to about 0.25 seconds) under the conditions employed. The bottom-most trace 1220 corresponds to the signal that was detected via the detection coil 1140 when the sample material was stationary, the excitation coil was used as an excitation coil, and the detection coil was used as a detection coil, as described above. This data trace 1220 shows a small or relatively minimal signal as the sample material is stationary, such that the sample material that was excited in the excitation region corresponding to the excitation coil 1130 remains in that region and thus is not detected in the detection region corresponding to the detection coil 1140.

The data trace 1230 corresponds to the signal that was detected when the sample material flow rate was the fastest, at 20 μL/min. This data trace 1230 shows some signal, with a peak in the signal 1240 centered at about 0.01 second. The next two data traces 1250 correspond to two signals that were detected, in separate runs, when the sample material flow rate was 10 μL/min. Each of these data traces 1250 shows a signal peak 1260 at about 0.02 second. The next several data traces 1270, 1290, and 1310 correspond to signals that were detected when the flow rate was 5 μL/min, 4 μL/min, and 3 μL/min, respectively. These data traces show signal peaks 1280, 1300, and 1320 at about 0.04 second, 0.05 second, and 0.06 second, respectively.

Data from the experiment may be viewed, interpreted, explained, generalized, or summed up in a number of ways. For example, as expected, a signal peak, corresponding to the arrival of the excited sample material in the detection coil, occurs earlier when the flow rate is higher and later when the flow rate is lower. Further, a signal peak is narrower when the flow rate is higher and wider when the flow rate is lower (compare peaks 1260 and 1280, for example), as the bolus of excited sample material moves more quickly in the former case and more slowly in the latter case through the detection region of the apparatus. Still further, a signal peak is higher in amplitude when the flow rate is higher and lower in amplitude when the flow rate is lower (compare peaks 1280, 1300, and 1320, for example). This may be attributed to signal decay over time, as may be appreciated in relation to the top-most trace 1210. An interesting aspect of the data is that it demonstrates that it is possible to capture the long-lived portion of a signal detected when sample material is flowing through the apparatus described above and the apparatus is operated as described above. It is noted that when the apparatus was employed as described above, with a conduit having an inner diameter of 100 μm and a sample material flowing at a rate of 10 μL/min, the bulk sample material velocity was 21 mm/sec. If the 100 μm-long detection coil had been used as a single coil in a dual-use excitation/detection mode, the excited sample material would have exited the coil in less than 0.005 second. In such a case, where the detection opportunity is so truncated, the detected signal would not have shown any long-lived portion and thus would not have been as useful.

Useful NMR-related apparatus, methods, and associated technology have been described herein. Same may be usefully employed in any of a variety of suitable NMR applications, such as NMR detection involving a flowing sample material, for example. Same may be usefully employed in any such NMR detection application, such as NMR detection involving the determination of the presence or absence of an object in a flowing sample material, for example. Same may be usefully employed to obtain data that is relatively clear and definitive, even in an NMR application involving a sample material that flows at a relatively fast rate, for example. Same may be designed or constructed to take advantage of any of the various aspects, features, and/or embodiments described herein. Additional aspects, features, embodiments, alternatives, benefits and advantages of the NMR-related apparatus, methods, and associated technology described herein may be appreciated from the description and related figures herein and may be employed in any appropriate or useful manner, as is fully contemplated herein.

Various modifications, processes, as well as numerous structures that may be applicable herein, as are fully contemplated herein, will be apparent. Various aspects, features or embodiments may have been explained or described in relation to understandings, beliefs, theories, underlying assumptions, and/or working or prophetic examples, although it will be understood that any particular understanding, belief, theory, underlying assumption, and/or working or prophetic example is not limiting. Although the various aspects and features may have been described with respect to various embodiments and specific examples herein, it will be understood that any of same is not limiting with respect to the full scope of the appended claims or other claims that may be associated with this application.

The invention claimed is:

1. An apparatus configured for detection of magnetic resonance in flowing sample material, comprising:
   a uniform sample conduit configured for containing a continuously flowing sample material, the uniform sample conduit comprising an excitation region and a detection region, each of which is located along a straight section of the uniform sample conduit, wherein the excitation region is operably coupled to the detection region and the excitation region is upstream of the detection region;
   a source of magnetic field configured to provide a substantially uniform magnetic field over a magnetic field region comprising the excitation region and the detection region;
   an excitation coil disposed within the magnetic field region and in the excitation region, the excitation coil configured for excitation of said continuously flowing sample material in the excitation region in order to generate magnetic resonance via excitation energy;
   a detection coil separate and distinct from the excitation coil, operably paired with the excitation coil disposed within the magnetic field region, and in the detection region, the detection coil configured for detection of magnetic resonance in flowing sample material in the detection region, wherein the excitation coil and the detection coil are on a micrometer scale from 100 micrometers to 530 micrometers;
   a transmitter operably coupled to the excitation coil and configured to transmit excitation energy to the excitation coil; and
   a receiver operably coupled to the detection coil and configured to continuously receive at least one magnetic resonance signal from the detection coil whereby a magnetic resonance signal from a flowing sample is continuously detectable within the uniform sample conduit.

2. The apparatus of claim 1, wherein the uniform sample conduit further comprises a separation region between the excitation region and the detection region and the magnetic field region comprises the separation region.

3. The apparatus of claim 1, the apparatus configured for the detection of magnetic resonance in flowing sample material comprising an object flowing through the uniform sample conduit.

4. An apparatus configured for detection of magnetic resonance in a flowing sample material, comprising:
   a uniform sample conduit configured for containing a continuously flowing sample material, the uniform sample conduit comprising a first excitation/detection region and a second excitation/detection region, each of which is located along a straight section of the uniform sample conduit, wherein the first excitation/detection region is operably coupled to the second excitation/detection region and the first excitation/detection region is upstream of the second excitation/detection region;
   a source of magnetic field configured to provide a substantially uniform magnetic field over a magnetic field region comprising the first excitation/detection region and the second excitation/detection region;
   a first excitation/detection coil disposed within the magnetic field region and within the first excitation/detection region, the first coil configured for excitation of said continuously flowing sample material in the first excitation/detection region in order to generate a magnetic resonance signal via excitation energy and configured for detection of the magnetic resonance signal within the continuously flowing sample material in the first excitation/detection region;
   a second excitation/detection coil separate and distinct from the first excitation/detection coil, also disposed within the magnetic field region, and within the second excitation/detection region, the second excitation/detection coil configured for excitation of continuously flowing sample material in the second excitation/detection region in order to generate a magnetic resonance signal via excitation energy and configured for detection of the magnetic resonance signal within the continuously flowing sample material in the second excitation/detection region, wherein the first excitation/detection coil and the second excitation/detection coil are sized on a micrometer scale from 100 micrometers to 530 micrometers in diameter;
   a first transmitter/receiver operably coupled to the first excitation/detection coil and configured to transmit excitation energy to the first excitation/detection coil and configured to receive at least one magnetic resonance signal from the first excitation/detection coil;
   a second transmitter/receiver operably coupled to the second excitation/detection coil and configured to transmit excitation energy to the second excitation/detection coil and configured to receive at least one magnetic resonance signal from the second excitation/detection coil;
   whereby a magnetic resonance signal from a flowing sample is continuously detectable within the uniform sample conduit and
   a coupler that is operably and electrically coupled to the first and the second excitation/detection coils.

5. The apparatus of claim 4, wherein the uniform sample conduit further comprises a separation region between the first excitation/detection region and the second excitation/detection region and the magnetic field region comprises the separation region.

6. The apparatus of claim 4, with the apparatus configured for a detection of magnetic resonance in a flowing sample material comprising:
   an object flowing through the uniform sample conduit, as the flowing sample material.

7. The apparatus of claim 4, further comprising a correlator providing a temporal correlation between at least one magnetic resonance signal from the first excitation/detection coil and at least one magnetic resonance signal from the second excitation/detection coil.

* * * * *